United States Patent
Lee et al.

(10) Patent No.: US 12,329,814 B2
(45) Date of Patent: *Jun. 17, 2025

(54) COMBINATION OF A SUBSTANCE MODULATING TUMOR IMMUNE MICROENVIRONMENT AND IMMUNOTHERAPY FOR THE TREATMENT OF CANCER

(71) Applicants: Boostimmune, Inc., Seoul (KR); The University of Tokyo, Tokyo (JP)

(72) Inventors: Gwanghee Lee, Busan (KR); Jeonghyun Ryou, Gyeonggi-do (KR); Jiwon Huh, Seoul (KR); Tadatsugu Taniguchi, Tokyo (JP); Sho Hangai, Tokyo (JP); Hideyuki Yanai, Tokyo (JP)

(73) Assignees: Boostimmune, Inc., Seoul (KR); THE UNIVERSITY OF TOKYO, Tokyo (JP)

( * ) Notice: Subject to any disclaimer, the term of this patent is extended or adjusted under 35 U.S.C. 154(b) by 90 days.

This patent is subject to a terminal disclaimer.

(21) Appl. No.: 17/854,739

(22) Filed: Jun. 30, 2022

(65) Prior Publication Data
US 2024/0000932 A1 Jan. 4, 2024

(51) Int. Cl.
*A61K 39/395* (2006.01)
*A61P 35/00* (2006.01)

(52) U.S. Cl.
CPC .... *A61K 39/39558* (2013.01); *A61K 39/3955* (2013.01); *A61P 35/00* (2018.01)

(58) Field of Classification Search
None
See application file for complete search history.

(56) References Cited

U.S. PATENT DOCUMENTS

2022/0155303 A1* 5/2022 Kim .................. G01N 33/5011

FOREIGN PATENT DOCUMENTS

WO 2012/080509 A1 6/2012

OTHER PUBLICATIONS

Xiao et al. (Extracellular translationally controlled tumor protein promotes colorectal cancer invasion and metastasis through Cdc42/JNK/ MMP9 signaling. Oncotarget. 2016;7(31):50057-50073). (Year: 2016).*
Julie Acunzo et al, "TCTP as therapeutic target in cancers", Cancer Treatment Reviews, 2014, pp. 760-769, vol. 40.

* cited by examiner

*Primary Examiner* — Peter J Reddig
*Assistant Examiner* — Sarah A Alsomairy
(74) *Attorney, Agent, or Firm* — Sughrue Mion, PLLC

(57) ABSTRACT

The present invention relates to a novel combination of (1) a substance that suppresses or inhibits the function of extracellular TCTP (translationally controlled tumor protein), especially released from tumor cells, and (2) a cancer immunotherapeutic agent for the treatment of cancer. Preferably, such a cancer immunotherapeutic agent is an immune checkpoint inhibitor. The substance that suppresses or inhibits the function of extracellular TCTP functions as an activator or enhancer of anti-tumor immune cells including T cells and natural killer (NK) cells and/or an antagonist of immunosuppressive cells, such as myeloid-derived suppressor cells (MDSCs), in the tumor immune microenvironment (TIME). The combination according to the present invention is useful for treating or preventing cancer. The combination according to the present invention is also useful for alleviating, reverting, or preventing immune suppression in the tumor immune microenvironment.

8 Claims, 23 Drawing Sheets

Specification includes a Sequence Listing.

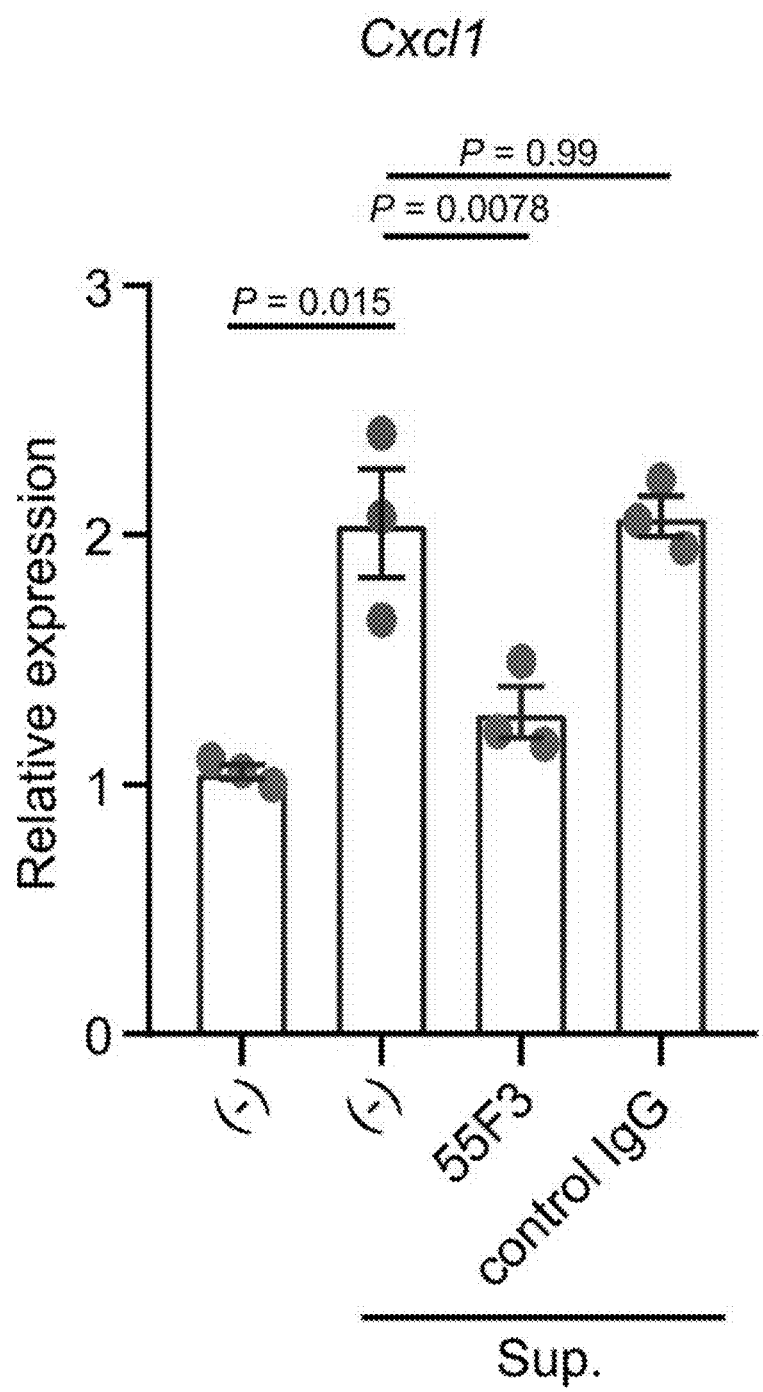

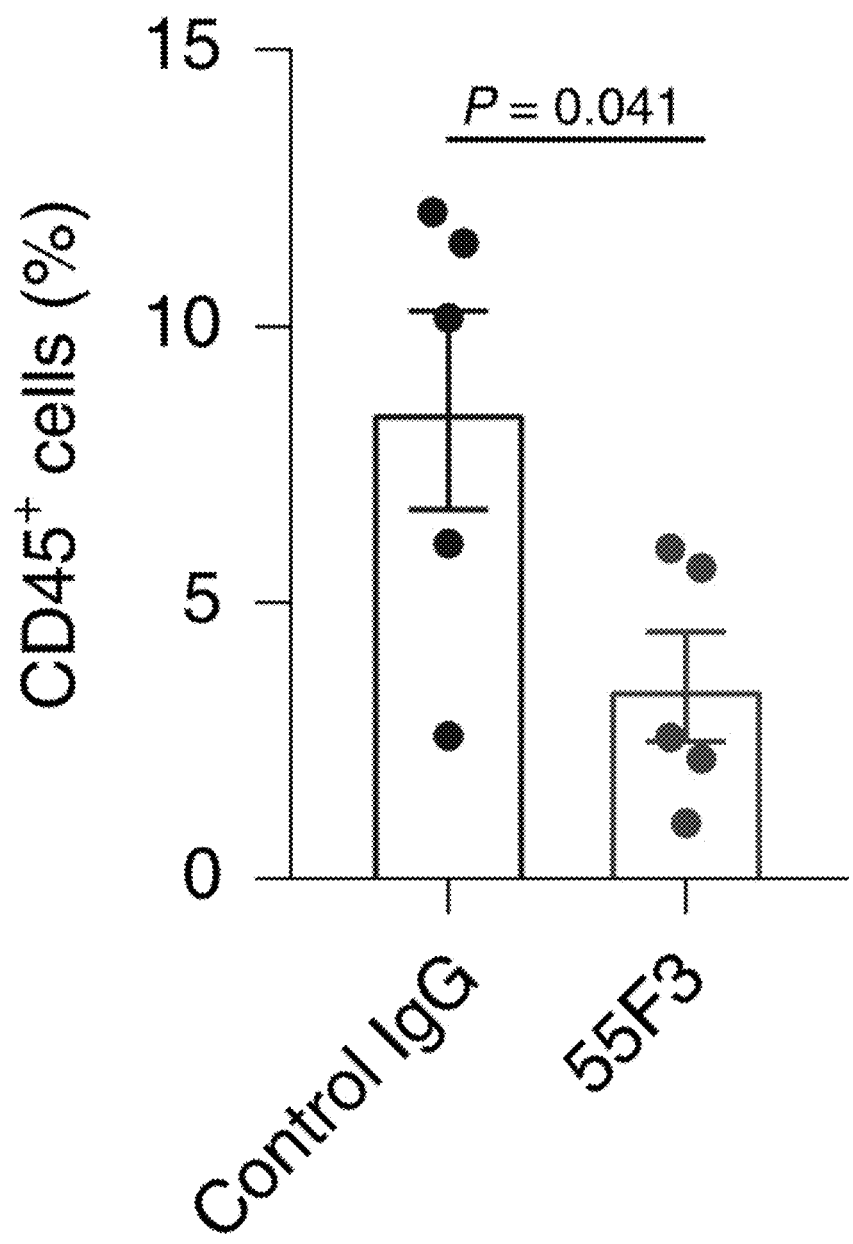

COMBINATION OF A SUBSTANCE MODULATING TUMOR IMMUNE MICROENVIRONMENT AND IMMUNOTHERAPY FOR THE TREATMENT OF CANCER

SEQUENCE LISTING

The content of the electronically submitted sequence listing, file name: Sequence_Listing_As_Filed.txt; size: 17,358 bytes; and date of creation: Jun. 29, 2022, filed herewith, is incorporated herein by reference in its entirety.

PARTIES TO A JOINT RESEARCH AGREEMENT

The subject matter disclosed in U.S. application Ser. No. 18/022,593 and the claimed invention were made by or on the behalf of parties to a joint research agreement that was in effect on or before the effective filing date the claimed invention, and the claimed invention was made as a result of activities undertaken within the scope of the joint research agreement. The parties to the joint research agreement are BOOSTIMMUNE, INC. and THE UNIVERSITY OF TOKYO.

FIELD OF THE INVENTION

The present invention relates to a novel combination of (1) a substance that suppresses or inhibits the function of extracellular TCTP (translationally controlled tumor protein), especially released from tumor cells, and (2) a cancer immunotherapeutic agent for the treatment of cancer. Preferably, such a cancer immunotherapeutic agent is an immune checkpoint inhibitor. The substance that suppresses or inhibits the function of extracellular TCTP functions as an activator or enhancer of anti-tumor immune cells including T cells and natural killer (NK) cells and/or an antagonist of immunosuppressive cells, such as myeloid-derived suppressor cells (MDSCs), in the tumor immune microenvironment (TIME). Preferably, the TCTP inhibitor according to the present invention is capable of inhibiting the accumulation of MDSCs in the TIME. Preferably, the substance that suppresses or inhibits the extracellular function of TCTP or its modified form, or a fragment or multimer thereof is an antibody, antigen-binding fragment, or binding molecule which specifically binds to TCTP. The present invention also relates to the use of said combination for treating or preventing cancer. The present invention also relates to the use of said combination for alleviating, reverting, or preventing immune suppression in the TIME.

BACKGROUND OF THE INVENTION

The tumor immune microenvironment (TIME) facilitates or inhibits growth of tumor cells via the interplay between tumor cells and surrounding cells. TIME contains a variety of cells, including fibroblasts, endothelial cells, mast cells, and other immune cells. Immune cells in the TIME include T lymphocytes, natural killer (NK) cells, tumor-associated macrophages (TAMs), dendritic cells (DCs), myeloid-derived suppressor cells (MDSCs), regulatory T cells (Tregs), and neutrophils. It has been known that a mechanism of suppressing an immune response to tumor cells exists in the TIME, which presents significant obstacles to cancer immunotherapy.

In recent years, therapeutic options for the treatment of cancers have changed with the development of immunotherapy that modulates immune responses against tumors. Among the various types of immunotherapies, immune checkpoint blockade covers a range of monoclonal antibody-based therapies that aim at blocking the interaction of immunomodulatory receptors (immune checkpoints) expressed on the surface of immune cells, with their ligands. Immune checkpoint inhibitors have shown significant clinical benefits, but unfortunately, there are still unmet clinical needs for the majority of patients who show no or limited responses. Analyses of patient populations treated with immune checkpoint inhibitors have revealed that there are classes of the TIME that are associated with tumors less prone to respond to immune checkpoint inhibitors.

TCTP is highly conserved in eukaryotic organisms. This protein, located both in the cytoplasmic and the nucleus, is expressed in various tissues and regulated in response to a wide range of extracellular stimuli. TCTP interacts with itself and other proteins including MCL1 and p53 (Acunzo et al., 2014). Strategies to inhibit the intracellular TCTP expression by nucleic acids targeting TCTP-encoding mRNAs, such as antisense oligonucleotides, siRNAs, and shRNAs, have been suggested (e.g., WO 2012/080509), but the function of TCTP outside the cells has not been well-established so far. Thus, provision of an antibody that suppresses or inhibits the function of extracellular TCTP, especially released from tumor cells, let alone its combination with cancer immunotherapy including immune checkpoint inhibitors, is novel.

BRIEF SUMMARY OF THE INVENTION

The present invention relates to a combination comprising (1) a substance that suppresses or inhibits the function of extracellular TCTP or its modified form, or a fragment or multimer thereof (hereinafter sometimes referred to as "the TCTP inhibitor according to the present invention") and (2) a cancer immunotherapeutic agent including an immune checkpoint inhibitor. In particular, the extracellular TCTP may have been released tumor cells. Tumor cells may have been under stress condition. Such tumor cells may be dead, damaged, or live tumor cells.

Preferably, the substance that suppresses or inhibits the function of extracellular TCTP or its modified form, or a fragment or multimer thereof, especially released from tumor cells, functions as an activator or enhancer of anti-tumor immune cells including T cells and NK cells and/or an antagonist of immunosuppressive cells, such as MDSCs, in the TIME. Preferably, the TCTP inhibitor according to the present invention inhibits the accumulation of MDSCs in the TIME.

The present invention is based on the discovery for the first time that TCTP released from tumor cells is a novel immunomodulator that controls the functions and/or dynamics of T cells, NK cells, and/or MDSCs in the TIME. Specifically, it has been found that depletion or blockade of extracellular TCTP by means of the depletion of the Tpt1 gene (encoding the TCTP protein; hereinafter interchangeably referred to as "the TCTP gene") or anti-TCTP monoclonal antibodies led to suppression of in vivo tumor growth, enhancement of T cells and NK cells, and inhibition of MDSC recruitment in the TIME. Such anti-tumor effects and biochemical/cellular changes were significant when the depletion or blockade of extracellular TCTP was in combination with an immune checkpoint inhibitor.

In another aspect, the present invention relates to a combination comprising (1) a substance that suppresses or inhibits the function of extracellular TCTP or its modified form, or a fragment or multimer thereof, especially released from tumor cells, and (2) a cancer immunotherapeutic agent (including an immune checkpoint inhibitor), wherein the substance that suppresses or inhibits the extracellular function of TCTP or its modified form, or a fragment or multimer thereof is an antibody, antigen-binding fragment, or binding molecule which specifically binds to TCTP or its modified form, or a fragment or multimer thereof (hereinafter sometimes collectively referred to as "the anti-TCTP antibody according to the present invention").

Preferably, the anti-TCTP antibody according to the present invention may comprise CDR-H1, CDR-H2, CDR-H3, CDR-L1, CDR-L2, and CDR-L3 as follows:
  a) CDR-H1 as represented by SEQ ID NO: 1, CDR-H2 as represented by SEQ ID NO: 2, CDR-H3 as represented by SEQ ID NO: 3, CDR-L1 as represented by SEQ ID NO: 4, CDR-L2 as represented by SEQ ID NO: 5, and CDR-L3 as represented by SEQ ID NO: 6;
  b) CDR-H1 as represented by SEQ ID NO: 7, CDR-H2 as represented by SEQ ID NO:8, CDR-H3 as represented by SEQ ID NO: 9, CDR-L1 as represented by SEQ ID NO: 10, CDR-L2 as represented by SEQ ID NO: 11, and CDR-L3 as represented by SEQ ID NO: 12;
  c) CDR-H1 as represented by SEQ ID NO: 13, CDR-H2 as represented by SEQ ID NO: 14, CDR-H3 as represented by SEQ ID NO: 15; CDR-L1 as represented by SEQ ID NO: 16, CDR-L2 as represented by SEQ ID NO: 17, and CDR-L3 as represented by SEQ ID NO: 18; and
  d) CDR-H1 as represented by SEQ ID NO: 19, CDR-H2 as represented by SEQ ID NO: 20, CDR-H3 as represented by SEQ ID NO: 21; CDR-L1 as represented by SEQ ID NO: 22, CDR-L2 as represented by SEQ ID NO: 23, and CDR-L3 as represented by SEQ ID NO: 24.

In another aspect, the present invention relates to a combination comprising (1) a substance that suppresses or inhibits the function of extracellular TCTP or its modified form, or a fragment or multimer thereof, especially released from tumor cells, and (2) a cancer immunotherapeutic agent, wherein the cancer immunotherapeutic agent is a substance that suppresses the function of an immune checkpoint protein. The immune checkpoint protein may be those expressed on T cells, NK cells, or other effector cells.

Preferably, the immune checkpoint protein may be selected from the group consisting of CTLA-4, PD-1, TIM3, LAG3, BTLA, TIGIT, VISTA, GITR, CD47, B24, CD160 and KIR. More preferably, the immune checkpoint protein may be CTLA-4 or PD-1.

The combination according to various aspects of the present invention is used for treating or preventing cancer. Preferably, the cancer is selected from the group consisting of colorectal cancer, melanoma, and fibrosarcoma.

The combination according to various aspects of the present invention is also useful for alleviating, reverting, or preventing immune suppression in the tumor immune microenvironment.

The present invention also relates to a method for treating or preventing cancer comprising administering a combination thereof—comprising (1) the TCTP inhibitor according to the present invention and (2) a cancer immunotherapeutic agent including an immune checkpoint inhibitor—to a patient in need thereof. In particular, the TCTP inhibitor suppresses or inhibits the function of TCTP or its modified form, or a fragment or multimer released from tumor cells in the TIME. Preferably, the TCTP inhibitor according to the present invention activates or enhances T cells and/or NK cells, and/or inhibits the accumulation of immunosuppressive cells, such as MDSCs, in the TIME.

The combination according to various aspects of the present invention is also useful in a patient who has shown or is likely to show no or limited response to immunotherapy for the treatment of cancer.

In various aspects of the present invention, the two main active substances for the combination according to the present invention, i.e., the TCTP inhibitor according to the present invention and a cancer immunotherapeutic agent, may be administered simultaneously or sequentially.

DESCRIPTION OF THE FIGURES

FIG. 5B shows the abundance ratios of PMN-MDSCs (CD11b$^+$Ly6C$^+$Ly6G$^+$) and M-MDSCs (CD11b$^+$Ly6C$^{high}$Ly6G$^-$) in the CD45$^+$ cell populations. FIG. 5C shows the abundance ratios of TAM (CD11b$^+$ F4/80$^+$) and DC (CD11b$^-$CD11c$^+$) in the CD45$^+$ cell populations.

FIG. 5D shows representative plots. FIG. 5E shows the abundance ratios of PMN-MDSCs (CD11b$^+$Ly6C$^+$Ly6G$^+$) and M-MDSCs (CD11b$^+$Ly6C$^{high}$Ly6G$^-$) in the CD45$^+$ cell populations.

FIG. 6A shows relative expressions of Cxcl1 mRNA in peritoneal exudate cells stimulated with culture supernatant of SL4 cells containing antibody 55F3 or control IgG. Sup stands for conditioned supernatant.

FIG. 6C shows the abundance ratios of PMN-MDSCs (CD11b$^+$Ly6C$^+$Ly6G$^+$) in the CD45$^+$ cell population from SL4 cells treated with antibody 55F3 or control IgG in C57BL/6 mice.

DETAILED DESCRIPTION OF THE INVENTION

Figure 1:
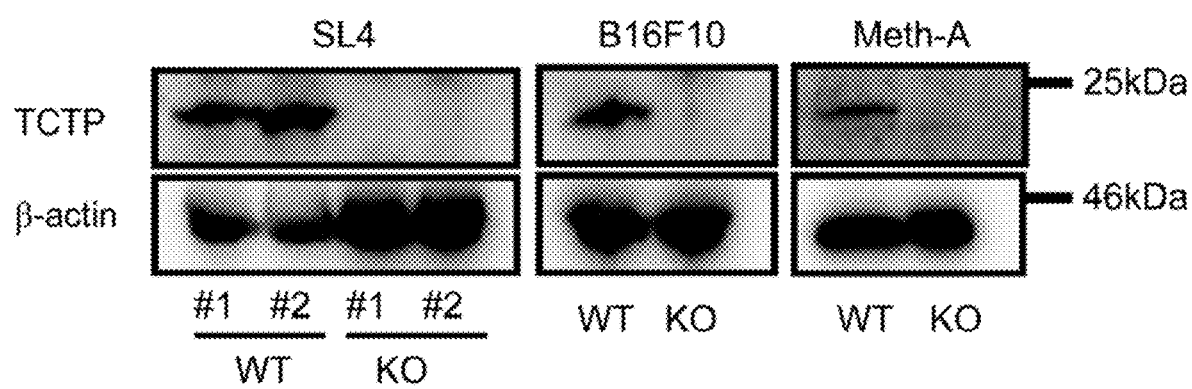
FIG. 1 shows the expression of TCTP in WT (wild-type) SL4, B16F10, and Meth-A cells, and TCTP KO (knock-out) SL4, B16F10, and Meth-A cells.

Although the present invention is described in details below, it is to be understood that this invention is not limited to the particular examples described herein. It is also to be understood that the terminology used herein is for the purpose of describing particular embodiments only and is not intended to limit the scope of the present invention which will be limited only by the appended claims. Unless defined otherwise, all technical and scientific terms used herein have the same meanings as commonly understood by one of ordinary skills in the art.

As used herein, the term "or" has the meaning of both "and" and "or" (i.e. "and/or"). Furthermore, the meaning of a singular noun includes that of a plural noun and thus a singular term, unless otherwise specified, may also carry the meaning of its plural form. In other words, the term "a" or "an" may mean one or more.

The present invention relates to a combination comprising (1) a substance that suppresses or inhibits the function of extracellular TCTP or its modified form, or a fragment or multimer thereof and (2) a cancer immunotherapeutic agent.

TCTP is also called histamine releasing factor (HRF), tumor protein translationally controlled 1 (Tpt1), p23 or fortilin. The amino acid and nucleic acid sequences are available on NCBI, accession no. CCDS9397.1 (cDNA) and NP_003286.1 (amino acids). As used herein, the term "TCTP" should be construed to include a fragment or multimer (e.g., dimer) of TCTP (which may be modified), as well as the full-length TCTP itself (which may be modified). The term "modified" as used herein may refer to any manipulation of the polypeptide backbone of TCTP (e.g., amino acid sequence) or any post-translational modifications (e.g., glycosylation or phosphorylation) of the TCTP polypeptide.

In particular, the extracellular TCTP targeted by the TCTP inhibitor according to the present invention may have been released from tumor cells. Tumor cells may have been stimulated or induced by stress.

Tumor cell proliferation can be stimulated or induced by various stimuli, which include intrinsic stress factors such as DNA damage or expression of tumor promoter genes, or extrinsic stress factors of various cell death inducers such as cytotoxic agents or radiation. Stress factors that can stimulate or induce tumor cells also may be diverse tumor-derived stresses, including reactive oxygen/nitrogen species-related stress, chronic inflammatory stress, hypoxia-related stress, endoplasmic reticulum stress, metabolic stress, and therapy-associated stress.

The tumor cells as used herein may be dead, damaged, or live tumor cells. The term "dead tumor cells" as used herein refer to tumor cells that have passed a point of no return in the death process and which changes cannot be reversed. Such tumor cells may have died through apoptosis or necrosis. The term "damaged tumor cells" as used herein may refer to tumor cells with a disrupted or ruptured cell membrane, or dying cells at a later stage of apoptosis or necrosis. Otherwise, tumor cells should be considered as live tumor cells, e.g., with an intact cell membrane. Conventional techniques, such as flow cytometry analysis or microscopic observation, may be used to determine if certain cells are dead, damaged, or live cells.

The TCTP inhibitor according to the present invention may function as an activator or enhancer of anti-tumor immune cells in the TIME. Preferably, such anti-tumor immune cells are tumor-killing cells, such as T cells and NK cells.

As used herein, the activation or enhancement of tumor-killing cells such as T cells and NK cells may be demonstrated by (1) the increase in the number of such cells or the level of cytokines that are upregulated when such cells have been activated (e.g., CD69), and/or (2) the suppression of tumor proliferation.

The term "activate," "activation," "activator," "enhance," "enhancement," or "enhancer" as used herein, means to induce or increase an activity or function by about 10%, 20%, 30%, 40%, 50%, 60%, 70%, 80%, 90%, or 100% or more in biological activity.

The TCTP inhibitor according to the present invention may also function as an antagonist of MDSCs, in the TIME. Preferably, the TCTP inhibitor according to the present invention inhibits the accumulation of MDSCs in the TIME.

As used herein, an antagonist of MDSCs is a substance capable of directly or indirectly reducing, suppressing, or inhibiting the immunosuppressive activity of MDSCs. The reduction, suppression, or inhibition of the immunosuppressive activity of MDSCs may be demonstrated by the inhibition of (1) accumulation or recruitment of MDSCs in the TIME, (2) activation of an immunomodulatory receptor (e.g., TLR2) on MDSCs, (3) release of an immunosuppressive cytokine (e.g., CXCL1/2) from MDSCs, and/or (4) tumor proliferation. Preferably, the TCTP inhibitor according to the present invention as an antagonist of MDSCs inhibits the accumulation of MDSCs in the TIME.

As used herein, the terms "inhibit" and "suppress" are used interchangeably and refer to any statistically significant decrease in biological activity, including full blocking of the activity. For example, "inhibition" can refer to a decrease of about 10%, 20%, 30%, 40%, 50%, 60%, 70%, 80%, 90% or 100% in biological activity.

Herein, the tumor immune microenvironment (TIME) means a site of interaction between cancer cells and non-cancer cells mainly including immune cells, and the tumor immune microenvironment is defined to be a microenvironment present in cancer, which in most cases comprises an environment advantageous for the survival of cancer.

MDSCs represent a heterogenous group of myeloid cells that account for a major component of immune cells in the TIME and are highly suppressive to anti-tumor lymphocyte function and trafficking to the tumor. Two major subsets of MDSCs have been identified: polymorphonuclear MDSCs (PMN-MDSCs) share phenotypic and morphologic features with neutrophils, whereas monocytic MDSCs (M-MDSCs) resemble monocytes and are known to differentiate to tumor-associated macrophages (TAMs). Elevated levels of MDSCs in almost all types of malignancies are directly correlated with more advanced clinical cancer stages, metastatic tumor burden, and poor prognosis (Jiang et al., 2015, Diaz-Montero et al., 2009, and Limagne et al., 2016). Despite their studies, the dynamics of MDSCs in the TIME still remains poorly understood. Accumulation of MDSCs in TIME means that MDSCs such as PMN-MDSCs are located in the TIME or around the TIME.

The present inventors have found that depletion or blockade of extracellular TCTP by means of the inactivation of the TCTP gene or anti-TCTP monoclonal antibodies can lead to suppression of in vivo tumor growth and MDSC recruitment in the TIME. The present inventors have also found that when TCTP as a molecule released from tumor cells acts on immune cells present in the TIME, cytokines such as CXCL1 and CXCL2 are significantly released from, in particular, M-MDSCs, among those immune cells. Moreover, it was found that CXCL1 and CXCL2 induce PMN-MDSCs into or around the TIME, mediated by CXCR2 present on the PMN-MDSCs. CXCL1 and CXCL2 have been known to regulate migration of hematopoietic cells such as MDSCs. It also has been known that the PMN-MDSCs induced into or around the TIME suppress the attack of immune cells such as T cells or NK cells against cancer cells (Kumar et al., 2016). The above-mentioned anti-tumor effects and biochemical/cellular changes were significant when the depletion or blockade of extracellular TCTP was in combination with an immune checkpoint inhibitor.

While not being bound by any mechanism, the anti-tumor activity of immune cells may be suppressed by accumulation of PMN-MDSCs in the TIME through the aforementioned TCTP-(M-MDSC)-CXCL1/2-(PMN-MDSC) pathway, so that tumor proliferation can be promoted. Accordingly, if immunosuppressive activities of MDSCs in the TIME were inhibited by suppressing or inhibiting the function of TCTP, accumulation or activation of T cells, NK cells, etc. could be promoted, and as a result, tumor proliferation could be inhibited or suppressed. Furthermore, such anti-tumor effects and biochemical/cellular changes can be augmented by the combination with an immune checkpoint inhibitor. The suppression or inhibition of the immunosuppressive activities of MDSCs may involve not only the reduced accumulation/recruitment of MDSCs in the TIME, but it also may involve any functional changes down-regulating immunosuppressive activities of MDSCs (e.g., down-regulation of signaling through its receptors such as TLR2 and CXCR2 or ligands such as CXCL1 and CXCL2) without a substantial change in the number of MDSCs. Herein, the function of TCTP may mean, for example, its ability to bind to a receptor thereof (e.g. TLR2), to induce the release of cytokines (e.g. CXCL1 and CXCL2) from cells (e.g. MDSCs, etc.), to inhibit the accumulation of MDSCs in the TIME, and/or to suppress tumor proliferation.

Examples of the substance that suppresses or inhibits the function of extracellular TCTP, especially released from tumor cells, may include, but are not limited to, antibodies, antigen-binding fragments thereof, and binding molecules that specifically bind to TCTP. Such binding molecules may include a bispecific antibody, an immunoconjugate, an antibody conjugated with a drug, an affibody, an adnectin, an ANTICALIN, a DARPin, a knottin, a peptide aptamer, or a fusion protein that specifically binds to TCTP.

As used herein, the term "immunotherapeutic agent" may include any molecule, peptide, antibody, a chimeric antigen receptor (CAR) or T cell receptor (TCR) based cell therapy or other agent which can stimulate a host immune system to generate an immune response to a tumor or cancer in the subject. Stimulation of a host immune system to generate an immune response to a tumor or cancer in the subject may be achieved by stimulating or inhibiting various immune cells or immunomodulatory proteins expressed thereon. Preferably, the immunotherapeutic agent to be used for the combination of the present invention is an immune checkpoint inhibitor.

As used herein, the immune checkpoint inhibitor means any substance (e.g., small molecule, protein, peptide, nucleic acid molecule, or antibody) that is administered to a patient to stimulate the patient's immune system by inhibiting an immunomodulatory protein called an immune checkpoint expressed on immune cells from binding with its partner protein. Immune checkpoint inhibitors may target any immune checkpoint known in the art that results in the stimulation of the immune system, including but not limited to, CTLA-4, PD-1, PD-L1, PD-L2, B7-H3, B7-H4, BTLA, HVEM, TIM3, GAL9, LAG3, CSF-1R, GITR, VISTA, KIR, 2B4, CD160, CGEN-15049, CHK1, CHK2, A2aR, ADAR1, CD47, ICOS, TIGIT and the B-7 family of ligands. Combinations of inhibitors for a single component of the immune checkpoints or different inhibitors for different components of the immune checkpoints may be used. Preferably, the immune checkpoint inhibitor is a substance that inhibits an immune checkpoint expressed on T cells, natural killer (NK) cells, or other immune cells (such as macrophages, dendritic cells (DCs), myeloid cells and neutrophils). More preferably, the immune checkpoint inhibitor inhibits an immune checkpoint molecule expressed on T cells. Immune checkpoints expressed on T cells include CD80 (67-1), PD-1 (CD279), CD28, CTLA-4 (CD152), ICOS (CD278), TMIGD2 (IGPR-1; CD28H), CD160, BTLA (CD272), HVEM (TNFRSF14; CD270), LAG3 (CD223), CD137 (TNFRSF9; 4-1BB), OX40 (TNFRSF4; CD134), CD27 (TNFRSF7), CD40L (TNFSF5; CD154), GITR (TNFRSF18; CD357), CD96, CD226 (DNAM-1), and TIGIT.

Preferably, the immune checkpoint inhibitor to be used in the combination according to the present invention is an anti-CTLA-4 antibody or anti-PD-1 antibody.

In an embodiment of the present invention, the immune checkpoint inhibitor is a CTLA-4 inhibitor. CTLA-4 (cytotoxic T-lymphocyte antigen 4) is a T lymphocyte surface protein with a major role in downregulation of the immune response. Examples of CTLA-4 inhibitors include antibodies that specifically bind to CTLA-4. Particular anti-CTLA-4 antibodies include, but are not limited to, ipilimumab, tremelimumab, quavonlimab, BMS-986249, zalifrelimab, ADG-126, ADG-116, BMS-986288, GIGA-564, CBT-509, and AGEN1181. Preference is given to ipilimumab or tremelimumab as anti-CTLA-4 antibody. For a general discussion of the availability, methods of production, mechanism of action, and clinical studies, see U.S. Pat. Nos. 6,984,720, 6,207,156, and Naido et al., 2014.

In an embodiment of the present invention, the immune checkpoint inhibitor is a PD-1 inhibitor. PD-1 (programmed cell death protein 1) is a cell surface receptor that is expressed on T regulatory and activated T cells (CD4 and CD8), activated B cells and NK cells. PD-1 binds PD-L1 and PD-L2, two ligands that are expressed by antigen-presenting cells and several cancer cells. Particular anti-PD-1 antibodies include, but are not limited to, nivolumab, pembrolizumab, pidilizumab, cemiplimab, spartalizumab, camrelizumab, sintilimab, tislelizumab, toripalimab, dostarlimab, sasanlimab, zimberelimab, prolgolimab, tebotelimab, retifanlimab, spartalizumab, nofazinlimab, cetrelimab, pimivalimab, AMP-224, and MEDI-0680. Preference is given to nivolumab or pembrolizumab or pidilizumab as anti-PD-1 antibody. For a general discussion of the availability, methods of production, mechanism of action, and clinical studies of anti-PD-1 antibodies, see U.S. 20130309250, U.S. Pat. Nos. 6,808,710, 7,595,048, 8,008,449, 8,728,474, 8,779, 105, 8,952,136, 8,900,587, 9,073,994, 9,084,776, and Naido et al., 2014.

In an embodiment of the present invention, the immune checkpoint inhibitor is a TIM3 inhibitor. TIM3 (T-cell immunoglobulin and mucin domain 3) is an immune checkpoint receptor that functions to limit the duration and magnitude of TH1 and TC1 T-cell responses. Examples of TIM3 inhibitors include antibodies that specifically bind to TIM3. Particular anti-TIM3 antibodies include, but are not limited to sabatolimab, cobolimab, Sym023, LY3321367, INCAGN2390, BMS-986258, SHR-1702, and R07121661. For a general discussion of the availability, methods of production, mechanism of action, and studies of TIM3 inhibitors, see U.S. 20150225457, U.S. 20130022623, U.S. Pat. No. 8,522,156, Ngiow et al., 2011, Ngiow, et al., 2011, and Anderson 2014.

In an embodiment of the present invention, the immune checkpoint inhibitor is a LAG3 inhibitor. LAG3 (lymphocyte activation gene 3) is a negative co-stimulatory receptor that modulates T cell homeostatis, proliferation, and activation. Examples of LAG3 inhibitors include antibodies that specifically bind to LAG3. Particular anti-LAG3 antibodies include, but are not limited to, relatlimab, LAG525, B1754111, Sym022, mavezelimab, TSR-033, INCAGN02385, LBL-007, FS118, R07247669, and EMB-02. For a general discussion of the availability, methods of production, mechanism of action, and studies, see, U.S. 20110150892, U.S. 20140093511, U.S. 20150259420, and Huang et al., 2004.

In an embodiment of the present invention, the immune checkpoint inhibitor is a BTLA inhibitor. BTLA (B- and T-lymphocyte attenuator) is a co-inhibitory receptor expressed by T lymphocytes and B lymphocytes that is important in regulating lymphocyte activation during inflammation and infection. Examples of BTLA inhibitors include antibodies that specifically bind to BTLA. Particular anti-BTLA antibodies include, but are not limited to, TAB004 and ANB032.

In an embodiment of the present invention, the immune checkpoint inhibitor is a TIGIT inhibitor. TIGIT is a co-inhibitory receptor expressed by regulatory T cells, activated CD8+ and CD4+ T cells, and natural killer (NK) cells. Examples of TIGIT inhibitors include antibodies that specifically bind to TIGIT. Particular anti-TIGIT antibodies include, but are not limited to, tiragolumab, vibostolimab, etigilimab, BMS-986207, domvanalimab, ASP8374, 1B1939, BGB-A1217, COM902, and M6223.

Preferably, the substance that suppresses or inhibits the function of extracellular TCTP, especially released from tumor cells, to be used in the combination according to the present invention is an antibody, an antigen-binding fragment thereof, or a binding molecule that specifically binds to TCTP.

The "antibody" as used herein is not particularly limited in terms of a preparation method thereof and a structure thereof, and examples of antibodies according to the present invention may include all "antibodies" that each bind to a desired antigen based on desired properties, such as, for example, a monoclonal antibody, a polyclonal antibody, a nanoantibody, a bispecific antibody, or an antibody conjugated with a drug.

The term "antigen binding fragment" refers to a molecule comprising a portion of an intact antibody, and in particular refers to a molecule comprising the antigenic determining variable regions of an intact antibody. It is known in the art that the antigen binding function of an antibody can be performed by fragments of a full-length antibody. Examples of antibody fragments include, but are not limited to, Fab, Fab', F(ab')2, and Fv fragments, linear antibodies, single chain antibodies, and multispecific antibodies formed from antibody fragments.

When the anti-TCTP antibody according to the present invention is a monoclonal antibody, the anti-TCTP antibody can be produced, for example, as follows. Examples of the method of producing a monoclonal antibody may include a hybridoma method (Kohler and Milstein 1975) and a recombination method (U.S. Pat. No. 4,816,567). Otherwise, the anti-TCTP antibody according to the present embodiment may be isolated from a phage antibody library (for example, Clackson et al., 1991; Marks et al., 1991; etc.) and the like. More specifically, when a monoclonal antibody is prepared by applying a hybridoma method, the preparation method includes, for example, the following 4 steps: (i) immunizing an animal to be immunized with an antigen, (ii) recovering monoclonal antibody-secreting (or potentially secreting) lymphocytes, (iii) fusing the lymphocytes with immortalized cells, and (iv) selecting cells that secrete a desired monoclonal antibody. Examples of the animal to be immunized that can be selected herein may include a mouse, a rat, a Guinea pig, a hamster, and a rabbit. After completion of the immunization, in order to establish hybridoma cells, lymphocytes obtained from a host animal are fused with an immortalized cell line, using a fusion agent such as polyethylene glycol, or an electrical fusion method. As fusion cells, for example, a rat or mouse myeloma cell line is used. After completion of the cell fusion, the cells are allowed to grow in a suitable medium containing a substrate that inhibits the growth or survival of unfused lymphocytes and immortalized cell line. According to an ordinary technique, parent cells that lack the enzyme, hypoxanthine-guanine phosphoribosyl transferase (HGPRT or HPRT), are used. From the thus obtained hybridomas, hybridomas generating desired antibodies are selected, and thereafter, a monoclonal antibody of interest can be obtained from a medium in which the selected hybridomas grow, according to an ordinary method.

The thus prepared hybridomas are cultured in vitro or are cultured in vivo in the ascites fluid of a mouse, a rat, a Guinea pig, a hamster, etc., and an antibody of interest can be then prepared from the culture supernatant, or from the ascites fluid.

Otherwise, the anti-TCTP antibody according to the present invention may be prepared by immunizing wild type or humanized mice (CAMOUSE®) and further performing single B cell screening by a Beacon platform (Ref. www.berkeleylights.com/systems/Beacon/, Rapid single B cell antibody discovery and structured light, mABs, doi.org/10.1080/19420862.2019.1624126). Single viable B cell arrays are prepared by applying mouse lymphocytes previously purified from spleen and/or lymph nodes of immunized mice to microarray chips. TCTP-specific antibody secreting single cells are screened on the microarray chip and then recovered by micromanipulation, mRNA are recovered from the single cells, and cDNA sequences encoding the variable regions of the IgG heavy (VH) and light (VL) chains are amplified by RT-PCR. The recombinant antibodies containing the VH and VL sequences are purified and tested by ELISA on TCTP.

Nanoantibody is a polypeptide consisting of a variable region of an antibody heavy chain (i.e., a variable domain of the heavy chain of heavy chain antibody (VHH)). In general, an antibody of a human or the like is composed of heavy and light chains. However, animals of family Camelidae, such as llamas, alpacas and camels, produce single-chain antibodies (heavy chain antibodies) consisting only of heavy chains. Such a heavy chain antibody can recognize a target antigen and can bind thereto, as in the case of a common antibody consisting of heavy and light chains. The variable region of a heavy chain antibody is the smallest unit that has a binding affinity to an antigen, and this variable region fragment is called a "nanoantibody." Nanoantibodies have high heat resistance, digestion resistance, and room temperature stability, and can be easily prepared in large quantities by a genetic engineering technique.

A nanoantibody can be produced, for example, as follows. An animal of family Camelidae is immunized with an antigen, and the presence or absence of an antibody of interest is then detected from the collected serum. Thereafter, cDNA is prepared from RNA derived from the peripheral blood lymphocytes of an immunized animal, in which a desired antibody titer is detected. A DNA fragment encoding VHH is amplified from the obtained cDNA, and the amplified DNA fragment is then inserted into a phagemid to prepare a VHH phagemid library. A desired nanoantibody can be prepared from the prepared VHH phagemid library through several screenings.

The anti-TCTP antibody according to the present invention may be a genetically engineered antibody. Such a genetically engineered antibody is not limited, and examples thereof may include a humanized antibody, and a chimeric antibody with a human antibody. The chimeric antibody is, for example, an antibody, in which a variable region derived from a different animal species is linked with a constant region derived from another different animal species (for example, an antibody, in which a variable region of a rat-derived antibody is bound to a constant region derived from a human) (for example, Morrison et al., 1984). The chimeric antibody can be easily constructed by genetic recombination technology.

The humanized antibody is an antibody that has a human-derived sequence in the framework region (FR) thereof and has a complementarity determining region (CDR) consisting of a sequence derived from another animal species (for example, a mouse, etc.). When such a humanized antibody is first explained using another animal species, for example, using a mouse, CDRs are transplanted from the variable regions of a mouse-derived antibody into human antibody variable regions, so that the heavy chain and light chain variable regions of the human antibody are reconstituted. Thereafter, the humanized reconstituted human antibody variable regions are ligated to humanized antibody constant regions, so that a humanized antibody can be produced. The method for producing such a humanized antibody is publicly known in the present technical field (e.g., Queen et al., 1989, etc.).

The antigen binding fragment of the anti-TCTP antibody according to the present invention is a partial region of the anti-TCTP antibody according to the present invention, which is an antibody fragment that binds to TCTP. Examples of such an antigen binding fragment may include Fab, Fab', F(ab')2, Fv (a variable fragment of an antibody), a single chain antibody (a heavy chain, a light chain, a heavy chain variable region, a light chain variable region, a nanoantibody, etc.), scFv (single chain Fv), a diabody (an scFv dimer), dsFv (disulfide-stabilized Fv), and a peptide comprising the CDR of the anti-TCTP antibody according to the present invention, at least, as a part thereof.

Fab is an antibody fragment having antigen-binding activity, in which about a half of the N-terminal side of a heavy chain and a light chain as a whole are bound to each other via a disulfide bond, among fragments obtained by treating an antibody molecule with the proteolytic enzyme papain. Such Fab can be produced by treating an antibody molecule with papain to obtain a fragment, and also, for example, by constructing a suitable expression vector into which DNA encoding Fab is inserted, then introducing this vector into suitable host cells (e.g., mammalian cells such as CHO cells, yeast cells, insect cells, etc.), and then allowing Fab to express in the cells.

F(ab')2 is an antibody fragment having antigen-binding activity, which is slightly larger than a fragment obtained by treating an antibody molecule with the proteolytic enzyme pepsin, in which Fab is bound via a disulfide bond in the hinge region. Such F(ab')2 can be produced by treating an antibody molecule with pepsin to obtain a fragment, or via a thioether bond or a disulfide bond, or further, by a genetic engineering technique, as in the case of Fab.

Fab' is an antibody fragment having antigen-binding activity, in which the disulfide bond in the hinge region of the above-described F(ab')2 is cleaved. Such Fab' can also be produced by a genetic engineering technique, as in the case of Fab.

scFv is a VH-linker-VL or VL-linker-VH polypeptide, in which one heavy chain variable region (VH) and one light chain variable region (VL) are linked to each other using a suitable peptide linker, and it is an antibody fragment having antigen-binding activity. Such ScFv can be produced by obtaining cDNAs encoding the heavy and light chain variable regions of an antibody, and then performing a genetic engineering technique.

Diabody is an antibody fragment having a divalent antigen-binding activity, in which scFv is dimerized. The divalent antigen-binding activity may be an identical antigen-binding activity, or one of them may be a different antigen-binding activity. Such a diabody can be produced by obtaining cDNAs encoding the heavy chain and light chain variable regions of an antibody, then constructing cDNA encoding scFv, in which the heavy chain variable region and the light chain variable region are linked to each other by a peptide linker, and then performing a genetic engineering technique.

DsFv refers to polypeptides, in which one amino acid residue in each of the heavy chain variable region and the light chain variable region is replaced with a cysteine residue, which are bound to each other via a disulfide bond between the cysteine residues. The amino acid residue to be replaced with the cysteine residue can be selected based on the prediction of the three-dimensional structure of the antibody.

Such dsFv can be produced by obtaining cDNAs encoding the heavy chain and light chain variable regions of an antibody, then constructing DNA encoding the dsFv, and then performing a genetic engineering technique.

A peptide comprising a CDR is configured to comprise at least one region of the CDRs (CDR1 to 3) of a heavy or a light chain. A plurality of peptides each comprising a CDR can be bound to one another, directly or via a suitable peptide linker. Such a peptide comprising a CDR can be produced by constructing DNA encoding the CDR of the heavy chain or light chain of an antibody, and inserting the constructed DNA into an expression vector. Herein, the type of the vector is not particularly limited, and it may be appropriately selected, depending on the types of host cells into which the vector is to be introduced, etc. Thereafter, the peptide comprising a CDR can be produced by introducing the expression vector comprising the DNA into suitable host cells (e.g. mammalian cells such as CHO cells, yeast cells, insect cells, etc.) for allowing it to express as an antibody. Alternatively, the peptide comprising a CDR can also be produced by a chemical synthesis method such as an Fmoc method (fluorenylmethyloxycarbonyl method) and a tBoc method (t-butyloxycarbonyl method).

In general, in the case of a human antibody (a complete human antibody), a hypervariable region that is the antigen binding site of a V region, other parts of the V region, and a constant region have the same structures as those of the antibody of a human. Such a human antibody can be easily produced by a person skilled in the art according to a known technique. The human antibody can be obtained by, for example, a method using a human antibody-producing mouse having a human chromosome fragment containing the H chain and L chain genes of the human antibody (e.g. Tomizuka et al., Proc. Natl. Acad. Sci. USA, 97, 722-727, 2000, etc.) or a method of obtaining a human antibody derived from a phage display selected from a human antibody library (see, for example, Siriwardena et al., Opthalmology, (2002) 109 (3), 427-431, etc.).

A multispecific antibody can be constructed using the antigen-binding fragment of the anti-TCTP antibody according to the present invention. Multispecificity means that an antibody has binding specificity to two or more antigens, and may be, for example, the form of a protein containing a monoclonal antibody having binding specificity to two or more antigens or an antigen-binding fragment thereof. Such multispecificity is achieved by a person skilled in the art according to a known technique. As methods of constructing multispecificity, there have been developed multiple methods, which are classified into a technique of constructing an asymmetric IgG, in which two different types of antibody heavy chain molecules are subjected to protein engineering operations so that they form a heterodimer, and a technique of ligating to each other, antigen-binding fragments each having a low molecular weight, which are obtained from an antibody, or ligating such an antigen-binding fragment to another antibody molecule. As an example of a specific construction method, the following publication can be, for example, referred to: Kontermann et al., Drug Discovery Today, 20, 838-847, 2015.

Examples of the anti-TCTP antibody according to the present invention and an antigen-binding fragment thereof may include antibodies, which are characterized in that the amino acid sequences of CDRs (complementarity determining regions) 1 to 3 satisfy any of the following (A), (B), (C), or (D), and antigen-binding fragments thereof.

(A) CDRs of 55F3 antibody have:
the amino acid sequence of heavy chain CDR1 (CDR-H1) that is GYSIASDYAWN (SEQ ID NO: 1),
the amino acid sequence of heavy chain CDR2 (CDR-H2) that is YINYSGSTGYNPSLKS (SEQ ID NO: 2),
the amino acid sequence of heavy chain CDR3 (CDR-H3) that is FEAGY (SEQ ID NO: 3),
the amino acid sequence of light chain CDR1 (CDR-L1) that is KASQDINRYLS (SEQ ID NO: 4),
the amino acid sequence of light chain CDR2 (CDR-L2) that is RANRLVD (SEQ ID NO: 5), and
the amino acid sequence of light chain CDR3 (CDR-L3) that is LQYNEFPLT (SEQ ID NO: 6).

(B) CDRs of 44E1 antibody have:
the amino acid sequence of heavy chain CDR1 (CDR-H1) that is GYTFTDHAIH (SEQ ID NO: 7),
the amino acid sequence of heavy chain CDR2 (CDR-H2) that is YISPGNGDLKYNEKFKG (SEQ ID NO: 8),
the amino acid sequence of heavy chain CDR3 (CDR-H3) that is GWTL (SEQ ID NO: 9),
the amino acid sequence of light chain CDR1 (CDR-L1) that is KSSQSLLYRSNQKNYLV (SEQ ID NO: 10),
the amino acid sequence of light chain CDR2 (CDR-L2) that is WAFTRES (SEQ ID NO: 11), and
the amino acid sequence of light chain CDR3 (CDR-L3) that is QQHYSYPWT (SEQ ID NO: 12).

(C) CDRs of 51A9 antibody have:
the amino acid sequence of heavy chain CDR1 (CDR-H1) that is GYSITSDYAWN (SEQ ID NO: 13),
the amino acid sequence of heavy chain CDR2 (CDR-H2) that is YINYSGSTGYNPSLKS (SEQ ID NO: 14),
the amino acid sequence of heavy chain CDR3 (CDR-H3) that is FEAGY (SEQ ID NO: 15),
the amino acid sequence of light chain CDR1 (CDR-L1) that is KASQDINSYLS (SEQ ID NO: 16),
the amino acid sequence of light chain CDR2 (CDR-L2) that is RANRLVD (SEQ ID NO: 17), and
the amino acid sequence of light chain CDR3 (CDR-L3) that is LQYYEFPLT (SEQ ID NO: 18).

(D) CDRs of 1-2-4 antibody have:
the amino acid sequence of heavy chain CDR1 (CDR-H1) that is SYAMH (SEQ ID NO: 19),
the amino acid sequence of heavy chain CDR2 (CDR-H2) that is WINAGNGNTKYSQKFQD (SEQ ID NO: 20),
the amino acid sequence of heavy chain CDR3 (CDR-H3) that is WVFDY (SEQ ID NO: 21),
the amino acid sequence of light chain CDR1 (CDR-L1) that is RSSQSLVHRDGNTYLS (SEQ ID NO: 22),
the amino acid sequence of light chain CDR2 (CDR-L2) that is KISNRFF (SEQ ID NO: 23), and
the amino acid sequence of light chain CDR3 (CDR-L3) that is MQATQFPHT (SEQ ID NO: 24).

Moreover, the anti-TCTP antibody according to the present invention and its antigen-binding fragment include: an antibody comprising any of heavy chain variable regions comprising the amino acid sequence as set forth in SEQ ID NO: 25, SEQ ID NO: 26, SEQ ID NO: 27, or SEQ ID NO: 28, an antibody comprising any of light chain variable regions comprising the amino acid sequence as set forth in SEQ ID NO: 29, SEQ ID NO: 30, SEQ ID NO: 31, or SEQ ID NO: 32, and antigen-binding fragments thereof; and an antibody consisting of an amino acid sequence having an amino acid sequence identity of about 70% or more, preferably, about 80% or more, about 81% or more, about 82% or more, about 83% or more, about 84% or more, about 85% or more, about 86% or more, about 87% or more, about 88% or more, or about 89% or more, more preferably, about 90% or more, about 91% or more, about 92% or more, about 93% or more, about 94% or more, about 95% or more, about 96% or more, about 97% or more, or about 98% or more, and most preferably about 99% or more, to the amino acid sequence of each of a heavy chain variable region and/or a light chain variable region that constitute the aforementioned antibodies, wherein the antibody specifically binds to TCTP, and an antigen-binding fragment thereof.

```
Heavy chain variable region of 55F3 antibody
                                  (SEQ ID NO: 25)
MRVLILLWLFTAFPGILSDVQLQESGPGLVKPSQSLSLTC

TATGYSIASDYAWNWIRQFPGNKLEWMGYINYSGSTGYNP

SLKSRISITRDTSKNQFFLQLNSVTTEDTATYYCARFEAG

YWGQGTTLTVSSAKTTPPSVYPLAPGSAAQTNSMVTLGCL

VKGYFPEPVT

Heavy chain variable region of 44E1 antibody
                                  (SEQ ID NO: 26)
MEWSWVFLFFLSVTTGVHSEVQLQQSDAELVKPGASVKIS

CKASGYTFTDHAIHWAKQKPEQGLEWIGYISPGNGDLKYN

EKFKGKATLTTDKSSSTAYMQLNSLTSEDSAVYFCKSGWT

LWGQGTTLTVSSAKTTPPSVYPLAPGSAAQTNSMVTLGCL

VKGYFPEPVT

Heavy chain variable region of 51A9 antibody
                                  (SEQ ID NO: 27)
MRVLILLWLFTAFPGILSDVQLQESGPGLVKPSQSLSLTC

TATGYSITSDYAWNWIRQFPGNKLEWMGYINYSGSTGYNP

SLKSRISITRDTSKNKFFLQLNSVTTEDTATYYCARFEAG

YWGQGTTLTVSSAKTTPPSVYPLAPGSAAQTNSMVTLGCL

VKGYFPEPVT

Heavy chain variable region of 1-2-4 antibody
                                  (SEQ ID NO: 28)
MDWTWRILFLVAAATGAHSQVQLVQSGAEVKKPGASVKVS

CKASGYTFFSYAMHWVRQAPGQRLEWMGWINAGNGNTKYS

QKFQDRVTITRDTSATTAYMELSSLRSEDTAVYYCASWVF

DYWGQGTPVTVSS

Light chain variable region of 55F3 antibody
                                  (SEQ ID NO: 29)
MDMRTPAQFLGILLLWFPGIKCDIKMTQSPSSMSASLGER

VTITCKASQDINRYLSWFQQKPGKSPKTLIYRANRLVDGV

PSRFSGSGSGQDYSLTISSLEYGDMGIYYCLQYNEFPLTF

GAGTKLELKRADAAPTVSIFPPSSEQLTSGGASVVCFLN

Light chain variable region of 44E1 antibody
                                  (SEQ ID NO: 30)
MDSQAQVLMLLLLWVSGTCGDIVMSQSPSSVVSVGEKVT

MSCKSSQSLLYRSNQKNYLVWYQLKPGQSPKLLIYWAFTR

ESGVPDRFTGSGSGTDFTLTISSVKAEDLAVYYCQQHYSY

PWTFGGGTKLEVKRADAAPTVSIFPPSSEQLTSGGASVVC

FLN

Light chain variable region of 51A9 antibody
                                  (SEQ ID NO: 31)
MDMRTPAQFLGILLLWFPGIKCDIKMTQSPSSMYASLGER

VTFTCKASQDINSYLSWFQQKPGKSPKTLIYRANRLVDGV

PSRFSGSGSGQDYSLTISSLDYEDMGIYYCLQYYEFPLTF

GAGTKLELKRADAAPTVSIFPPSSEQLTSGGASVVCFLN

Light chain variable region of 1-2-4 antibody
                                  (SEQ ID NO: 32)
MRLLAQLLGLLMLWVPGSSGDIVMTQTPLSSLVTLGQPAS

ISCRSSQSLVHRDGNTYLSWLQQRPGQPPRLLIYKISNRF

FGVPDRFSGSGAGTDFTLKISRVEAEDVGVYYCMQATQFP

HTFGQGTKLEIK
```

Furthermore, the anti-TCTP antibody according to the present invention also includes an antibody that competitively inhibits the binding of the antibody to TCTP characterized in that the amino acid sequences of CDRs (complementarity determining regions) satisfy any of the above-described (A), (B), (C), or (D) to TCTP, and that suppresses or inhibits the function of TCTP. Such a competitive antibody can be prepared and obtained by a competitive experiment and the like that are publicly known to a person skilled in the art. Specifically, when the binding of a first anti-TCTP antibody to TCTP is competitively inhibited by a second anti-TCTP antibody, it is judged that the first anti-TCTP antibody and the second anti-TCTP antibody bind to a substantially identical antigen site, or that they bind to antigen sites that are extremely close to each other. When the second anti-TCTP antibody suppresses or inhibits the function of TCTP, the second anti-TCTP antibody is the competitive antibody according to the present embodiment and is included in the anti-TCTP antibody according to the present invention. Besides, as a method of the above-described competitive experiment, for example, a method of using a Fab fragment or the like is generally carried out in the present technical field. See, for example, WO 95/11317, WO 94/07922, WO 2003/064473, WO 2008/118356, WO 2004/046733, etc., the contents of which are incorporated by reference. Moreover, whether or not the second anti-TCTP antibody suppresses or inhibits the function of TCTP can be easily confirmed by the method disclosed herein.

The combination according to the present invention is useful for treating or preventing cancer (including malignant tumor/malignant neoplasm).

Examples of the cancer as a preventive or therapeutic target of the preventive or therapeutic method of the present invention may include hepatocellular carcinoma, bile duct cell carcinoma, renal cell carcinoma, squamous cell carcinoma, basal cell carcinoma, transitional cell carcinoma, adenocarcinoma, gastrinoma, melanoma, fibrosarcoma, myxosarcoma, liposarcoma, leiomyosarcoma, rhabdomyosarcoma, teratoma, angiosarcoma, Kaposi's sarcoma, osteosarcoma, chondrosarcoma, lymphangiosarcoma, meningioma, non-Hodgkin lymphoma, Hodgkin lymphoma, leukemia, brain tumor, head-and-neck cancer, epithelial cell-derived neoplasm (epithelial carcinoma), basal cell carcinomas, adenocarcinomas, lip cancer, oral cancer, esophageal cancer, gastrointestinal cancer such as small bowel cancer and stomach cancer, colon cancer, rectal cancer, hepatic cancer, bladder cancer, pancreatic cancer, ovarian cancer, cervical cancer, endometrial cancer, lung cancer, breast cancer, thyroid cancer, skin cancers such as squamous cell carcinoma and basal cell carcinoma, prostate cancer, and renal cell carcinoma. In addition, examples of the cancer may also include known other cancers that affect the epithelium, mesenchyme, and blood cells in the whole body. Preferably, the cancer is colorectal cancer, melanoma, or fibrosarcoma.

The term "treat" or "treatment" refers to the medical management of a patient with the intent to cure, ameliorate, stabilize, or prevent a disease, pathological condition, or disorder.

The term "prevent" or "prevention" refers to a treatment that forestalls or slows the onset of a disease or condition or reduced the severity of the disease or condition.

Thus, if a treatment can treat a disease in a subject having symptoms of the disease, it can also prevent that disease in a subject who has yet to suffer some or all of the symptoms.

The combination according to the present invention is also useful for alleviating, reverting or preventing immune suppression in the TIME.

Tumors employ multiple strategies to attenuate immune responses, which include accumulation of immunosuppressive cells or up-regulation of immunosuppressive cytokines or chemokines in the TIME. Such immunosuppressive cells include tumor-associated macrophages (TAMs), marrow-derived suppressor cells (MDSCs), tumor-associated neutrophils (TANs), cancer-associated fibroblasts (CAFs), and regulatory T cells (Tregs). Immunosuppressive cytokines and chemokines secreted into the TIME include CCL2, CCL3, CCL5, CCL17, CCL19, CCL21, CCL22, CCL28, CXCL5, CXCL8, CXCL12, CXCL15, CXCL17, MIF, HMGB1, CSF, CSF2, IL-4, IL-6, IL-10, IL-13, G-CSF, PGE2, and TGF-6. Herein, "alleviating, reverting or preventing immune suppression in the TIME" means that the accumulation of an immunosuppressive cell is inhibited or the activity of an immunosuppressive cytokine or chemokine in the TIME is downregulated. Preferably, the alleviation reversion, or prevention of immune suppression in the TIME exhibited by the combination according to the present invention may be demonstrated by activation/enhancement of T cells and/or NK cells or suppressed accumulation of MDSCs, preferably PMN-MDSCs, in the TIME.

Based upon standard laboratory techniques known to evaluate substances useful for the treatment of hyper-proliferative disorders such as cancer, by standard toxicity tests and by standard pharmacological assays for the determination of treatment of the conditions identified above in mammals, and by comparison of these results with the results of known medicaments that are used to treat these conditions, the effective dosage of the substances to be used in the combination of the present invention can readily be determined for treatment of each desired indication. The amount of the active ingredient to be administered in the treatment of one of these conditions can vary widely according to such considerations as the particular substance and dosage unit employed, the mode of administration, the period of treatment, the age and sex of the patient treated, and the nature and extent of the condition treated.

"Combination" means for the purposes of the present invention not only a dosage form which contains all the components (so-called fixed combinations), and combination packs containing the components separate from one another, but also components which are administered simultaneously or sequentially, as long as they are employed for the prophylaxis or treatment of the same disease.

The individual components of the combination as described herein may be administered either sequentially or simultaneously in separate or combined pharmaceutical formulations/compositions. Thus, (1) a substance that suppresses or inhibits the function of extracellular TCTP, especially released from tumor cells, and (2) a cancer immunotherapeutic agent (including an immune checkpoint inhibitor) may for example, be formulated separately and presented in separate packs or devices, or said individually formulated components may be presented in a single kit or pack.

The present invention further provides the use of the combination thereof for the preparation of a pharmaceutical composition for the treatment of the disorders described herein.

Such pharmaceutical compositions comprise a therapeutically effective amount of the active substance(s) dissolved or dispersed in a pharmaceutically acceptable excipient. "Pharmaceutical or pharmacologically acceptable" refers to molecular entities and compositions that are generally non-toxic to recipients at the dosages and concentrations employed, i.e. do not produce an adverse, allergic or other untoward reaction when administered to an animal, such as, for example, a human, as appropriate. The preparation of a pharmaceutical composition that contains either or both of two active substances according to the present invention— (1) the TCTP inhibitor according to the present invention and (2) a cancer immunotherapeutic agent—and optionally an additional active ingredient will be known to those of skill in the art in light of the present disclosure, as exemplified by Remington's Pharmaceutical Sciences, 18th Ed. Mack Printing Company, 1990, incorporated herein by reference. In particular, the compositions are lyophilized formulations or aqueous solutions. As used herein, "pharmaceutically acceptable excipient" includes any and all solvents, buffers, dispersion media, coatings, surfactants, antioxidants, preservatives, isotonic agents, salts, stabilizers and combinations thereof, as would be known to one of ordinary skill in the art.

The pharmaceutical compositions may be parenteral compositions, which include those designed for administration by injection, e.g. subcutaneous, intradermal, intralesional, intravenous, intraarterial intramuscular, intrathecal or intraperitoneal injection. For injection, either or both of the two active substances according to the present invention—(1) the TCTP inhibitor according to the present invention and (2) a cancer immunotherapeutic agent—may be formulated in aqueous solutions, preferably in physiologically compatible buffers such as Hanks' solution, Ringer's solution, or physiological saline buffer. The solution may contain formulary agents such as suspending, stabilizing and/or dispersing agents. Alternatively, the composition may be in powder form for constitution with a suitable vehicle, e.g., sterile pyrogen-free water, before use. Suitable pharmaceutically acceptable excipients include, but are not limited to, buffers such as phosphate, citrate, and other organic acids; antioxidants; preservatives; low molecular weight (less than about 10 residues) polypeptides; proteins, such as serum albumin, gelatin, or immunoglobulins; hydrophilic polymers such as polyvinylpyrrolidone; amino acids; monosaccharides, disaccharides, and other carbohydrates such as glucose, mannose, or dextrins; chelating agents; sugars; salt-forming counter-ions such as sodium; metal complexes (e.g. Zn-protein complexes); and/or non-ionic surfactants such as polyethylene glycol (PEG). Aqueous injection suspensions may contain compounds which increase the viscosity of the suspension, such as sodium carboxymethyl cellulose, sorbitol, dextran, or the like. Optionally, the suspension may also contain suitable stabilizers or agents which increase the solubility of the compounds to allow for the preparation of highly concentrated solutions. Additionally, suspensions of the active substances may be prepared as appropriate oily injection suspensions. Suitable lipophilic solvents or vehicles include fatty oils such as sesame oil, or synthetic fatty acid esters, such as ethyl cleats or triglycerides, or liposomes.

The present invention also relates to a method for treating or preventing cancer (including malignant tumor/malignant neoplasm). This method comprises administering the combination thereof to a patient in need thereof.

Examples of the cancer as a preventive or therapeutic target of the preventive or therapeutic method of the present invention may include hepatocellular carcinoma, bile duct cell carcinoma, renal cell carcinoma, squamous cell carcinoma, basal cell carcinoma, transitional cell carcinoma, adenocarcinoma, gastrinoma, melanoma, fibrosarcoma, myxosarcoma, liposarcoma, leiomyosarcoma, rhabdomyosarcoma, teratoma, angiosarcoma, Kaposi's sarcoma, osteosarcoma, chondrosarcoma, lymphangiosarcoma, meningioma, non-Hodgkin lymphoma, Hodgkin lymphoma, leukemia, brain tumor, head-and-neck cancer, epithelial cell-derived neoplasm (epithelial carcinoma), basal cell carcinomas, adenocarcinomas, lip cancer, oral cancer, esophageal cancer, gastrointestinal cancer such as small bowel cancer and stomach cancer, colon cancer, rectal cancer, hepatic cancer, bladder cancer, pancreatic cancer, ovarian cancer, cervical cancer, endometrial cancer, lung cancer, breast cancer, thyroid cancer, skin cancers such as squamous cell carcinoma and basal cell carcinoma, prostate cancer, and renal cell carcinoma. In addition, examples of the cancer may also include known other cancers that affect the epithelium, mesenchyme, and blood cells in the whole body. Preferably, the cancer is colorectal cancer, melanoma, or fibrosarcoma.

In another aspect of the present invention, the substance that inhibits the function of extracellular TCTP or its modified form, or a fragment or multimer thereof, especially released from tumor cells, may alleviate, revert, or prevent immune suppression in the tumor immune microenvironment.

Herein, "alleviates, reverts, or prevents immune suppression in the TIME" means that the number and/or activity of anti-tumor immune cells is increased, the accumulation of an immunosuppressive cell is inhibited the activity of an immunosuppressive cytokine or chemokine in the TIME is downregulated. Preferably, the alleviation, reversion or prevention of immune suppression in the TIME exhibited by the combination according to the present invention is demonstrated by increased activity and/or number of T cells or NK cells or suppressed accumulation of MDSCs, preferably PMN-MDSCs, in the TIME.

In another aspect of the present invention, the patient has shown or is likely to show no or limited response to immunotherapy for the treatment of cancer.

The term "immunotherapy" refers to the treatment of a subject afflicted with, or at risk of contracting or suffering a recurrence of, a disease by a method comprising inducing, enhancing, suppressing or otherwise modifying an immune response. Immune checkpoint inhibitors are a type of immunotherapy.

As used herein, the term "response" may refer to an alteration in a subject's condition that occurs as a result of or correlates with treatment. In some embodiments, a response is or comprises a beneficial response. In some embodiments, a beneficial response may include stabilization of the condition (e.g., prevention or delay of deterioration expected or typically observed to occur absent the treatment), amelioration (e.g., reduction in frequency and/or intensity) of one or more symptoms of the condition, and/or improvement in the prospects for cure of the condition, etc. In some embodiments, "response" may refer to response of an organism, an organ, a tissue, a cell, or a cell component or in vitro system. In some embodiments, a response is or comprises a clinical response. In some embodiments, presence, extent, and/or nature of response may be measured and/or characterized according to particular criteria; in some embodiments, such criteria may include clinical criteria and/or objective criteria. In some embodiments, techniques for assessing response may include, but are not limited to, clinical examination, positron emission tomography, chest X-ray CT scan, MRI, ultrasound, endoscopy, laparoscopy, presence or level of a particular marker in a sample, cytology, and/or histology. Where a response of interest is or comprises response of a tumor to therapy, those of ordinary skill will be aware of a variety of established techniques for assessing such response, including, for example, for determining tumor burden, tumor size, tumor stage, etc. For example, certain technologies for assessing response of solid tumors to treatment are discussed in Therasse et al., "New guidelines to evaluate the response to treatment in solid tumors", European Organization for Research and Treatment of Cancer, National Cancer Institute of the United States, National Cancer Institute of Canada, J. Natl. Cancer Inst., 2000, 92(3):205-216. Those of ordinary skill in the art will be aware of, and/or will appreciate in light of the present disclosure, strategies for determining particular response criteria for individual tumors, tumor types, patient populations or cohorts, etc, as well as for determining appropriate references therefor.

Hereinafter, the present invention will be further described in the following examples. However, these examples are only illustrative examples of the embodiments of the present invention, and thus, are not intended to limit the scope of the present invention.

EXAMPLES

Example 1: Preparation of TCTP Knock-Out (KO) Cell Line

TCTP KO SL4 cells, TCTP KO B16F10 cells, and TCTP KO Meth-A cells were produced by CRISPR/Cas9 genome editing using the CRISPR design tool (www.genome-engineering.org, accessed May 2017). The mouse melanoma cell line B16F10 cells and the mouse fibrosarcoma cell line Meth-A cells were obtained from RIKEN BioResource Center (Japan). The mouse colon carcinoma cell line SL4 was obtained from Juntendo University (Japan). Hereinafter, TCTP-sufficient cells without CRISPR/Cas9-mediated TCTP gene inactivation are referred to as wild-type (WT) cells, while TCTP-deficient cells with CRISPR/Cas9-mediated TCTP gene inactivation are referred to as knock-out (KO) cells.

The genomic sequences of the TCTP gene (5'-CGGGCG-GAAAAGGCCGACGC-3' (SEQ ID NO: 33) and 5'-AGGCCCGCCATTTCCCGCGC-3' (SEQ ID NO: 34)) were targeted. The first exon of the TCTP gene was flanked by the above two sequences, SEQ ID NO: 33 and SEQ ID NO: 34. Oligonucleotides corresponding to these guide sequences were cloned into the BbsI sites of pSpCas9(BB)-2A-GFP (PX458) (Addgene) and pSpCas9(BB)-2A-Puro (PX459) V2.0 (Addgene), respectively. The expression vector constructs were both introduced into SL4 cells. The construct-introduced cells were first selected with puromycin, and then they were subjected to single cell sorting using FACSAria II (BD Biosciences) or SH800S (SONY).

TCTP protein expression in SL4, B16F10 and Meth-A cells without (WT) or with CRISPR/Cas9-mediated TCTP gene inactivation (KO) was confirmed from the whole cell lysates of each cell lines (FIG. 1).

Example 2: Preparation of Anti-TCTP Monoclonal Antibody

Example 2-1: Mouse Monoclonal Antibody (55F3, 44E1, 51A9)

Mouse monoclonal antibodies reacting against TCTP were prepared according to a standard hybridoma technology. BALB/c mice were immunized with a synthetic peptide (EDGVTPYMIFFKDGLEMEKC; SEQ ID NO: 35) that is a partial sequence of human TCTP.

Antibodies were screened based on an immunoblotting analysis and an immunoprecipitation analysis against TCTP. As a result, antibodies 55F3, 44E1 and 51A9 were obtained.

The variable region sequences of the selected antibodies are as follows:

TABLE 1

| Heavy chain variable region sequences | |
|---|---|
| Antibody | Heavy chain variable region |
| 55F3 | MRVLILLWLFTAFPGILSDVQLQES GPGLVKPSQSLSLTCTATGYSIASD YAWNWIRQFPGNKLEWMGYINYSGS TGYNPSLKSRISITRDTSKNQFFLQ LNSVTTEDTATYYCARFEAGYWGQG TTLTVSSAKTTPPSVYPLAPGSAAQ TNSMVTLGCLVKGYFPEPVT (SEQ ID NO: 25) |
| 44E1 | MEWSWVFLFFLSVTTGVHSEVQLQQ SDAELVKPGASVKISCKASGYTFTD HAIHWAKQKPEQGLEWIGYISPGNG DLKYNEKFKGKATLTTDKSSSTAYM QLNSLTSEDSAVYFCKSGWTLWGQG TTLTVSSAKTTPPSVYPLAPGSAAQ TNSMVTLGCLVKGYFPEPVT (SEQ ID NO: 26) |
| 51A9 | MRVLILLWLFTAFPGILSDVQLQES GPGLVKPSQSLSLTCTATGYSITSD YAWNWIRQFPGNKLEWMGYINYSGS TGYNPSLKSRISITRDTSKNKFFLQ LNSVTTEDTATYYCARFEAGYWGQG TTLTVSSAKTTPPSVYPLAPGSAAQ TNSMVTLGCLVKGYFPEPVT (SEQ ID NO: 27) |

TABLE 2

| Light chain variable region sequences | |
|---|---|
| Antibody | Light chain variable region |
| 55F3 | MDMRTPAQFLGILLLWFPGIKCDIK MTQSPSSMSASLGERVTITCKASQD INRYLSWFQQKPGKSPKTLIYRANR LVDGVPSRFSGSGSGQDYSLTISSL EYGDMGIYYCLQYNEFPLTFGAGTK LELKRADAAPTVSIFPPSSEQLTSG GASVVCFLN (SEQ ID NO: 29) |
| 44E1 | MDSQAQVLMLLLLWVSGTCGDIVMS QSPSSPVVSVGEKVTMSCKSSQSLL YRSNQKNYLVWYQLKPGQSPKLLIY WAFTRESGVPDRFTGSGSGTDFTLT ISSVKAEDLAVYYCQQHYSYPWTFG GGTKLEVKRADAAPTVSIFPPSSEQ LTSGGASVVCFLN (SEQ ID NO: 30) |
| 51A9 | MDMRTPAQFLGILLLWFPGIKCDIK MTQSPSSMYASLGERVTFTCKASQD INSYLSWFQQKPGKSPKTLIYRANR LVDGVPSRFSGSGSGQDYSLTISSL DYEDMGIYYCLQYYEFPLTFGAGTK LELKRADAAPTVSIFPPSSEQLTSG GASVVCFLN (SEQ ID NO: 31) |

Example 2-2: Human Monoclonal Antibody (1-2-4)

Transgenic mice for preparing fully human antibodies (CAMOUSE®) were immunized by using a recombinant human TCTP (SEQ ID NO: 36), and standard single B cell screening method was used. Single viable B cell arrays were prepared by applying splenocyte of immunized mice to microarray chips. TCTP-specific antibody secreting single cells were screened on the microarray chip using human TCTP coated beads and then recovered by micromanipulation, mRNA were recovered from the single cells, and cDNA sequences encoding the variable regions of the IgG heavy (VH) and light (VL) chains were amplified by RT-PCR. The recombinant antibodies containing the VH and VL sequences are purified and tested by ELISA on TCTP. As a result, antibody 1-2-4 was obtained. The variable region sequences of antibody 1-2-4 are as follows. The antibody sequences for 1-2-4 were obtained from CAMOUSE® in cooperation with CAMAB (China) and GenScript (China).

TABLE 3

| Heavy chain variable region sequences | |
|---|---|
| Antibody | Heavy chain variable region |
| 1-2-4 | MDWTWRILFLVAAATGAHSQVQLVQS GAEVKKPGASVKVSCKASGYTFFSY AMHWVRQAPGQRLEWMGWINAGNGN TKYSQKFQDRVTITRDTSATTAYME LSSLRSEDTAVYYCASWVFDYWGQG TPVTVSS(SEQ ID NO: 28) |

TABLE 4

| Light chain variable region sequences | |
|---|---|
| Antibody | Light chain variable region |
| 1-2-4 | MRLLAQLLGLLMLWVPGSSGDIVMT QTPLSSLVTLGQPASISCRSSQSLV HRDGNTYLSWLQQRPGQPPRLLIYK ISNRFFGVPDRFSGSGAGTDFTLKI SRVEAEDVGVYYCMQATQFPHTFGQ GTKLEIK (SEQ IDNO: 32) |

Example 3: Effect of TCTP on Tumor Proliferation

To evaluate the effect of TCTP on tumor proliferation in vivo, a human TCTP gene was introduced into TCTP KO SL4 cells to generate the so-called knock-in cells.

HEK293Ta cells ($3\times10^6$ cells) were transfected with pCSII-EF-MCS-IRES2-Venus-hTCTP lentiviral expression vector and its helper vectors (pMDLg/p.RRE and pCMV-VSV-G-RSV-Rev). After 48 hours of the transfection, culture supernatants were collected and filtered (0.45 µm; Millipore). TCTP KO SL4 cells from Example 1 ($1\times10^6$ cells) were infected using the supernatant. After infection, GFP-positive human TCTP-expressing TCTP KO SL4 cells (hereafter TCTP KI SL4 cells) were sorted using FACS-Melody cell sorter. TCTP KI SL4 cells ($2\times10^5$ cells/100 µL PBS), TCTP KO SL4 cells ($2\times10^5$ cells/100 µL PBS), or parental SL4 cells ($2\times10^5$ cells/100 µL PBS) were inoculated into C57BL/6 mice. After cell inoculation, tumor volumes were measured over time.

Figure 2:
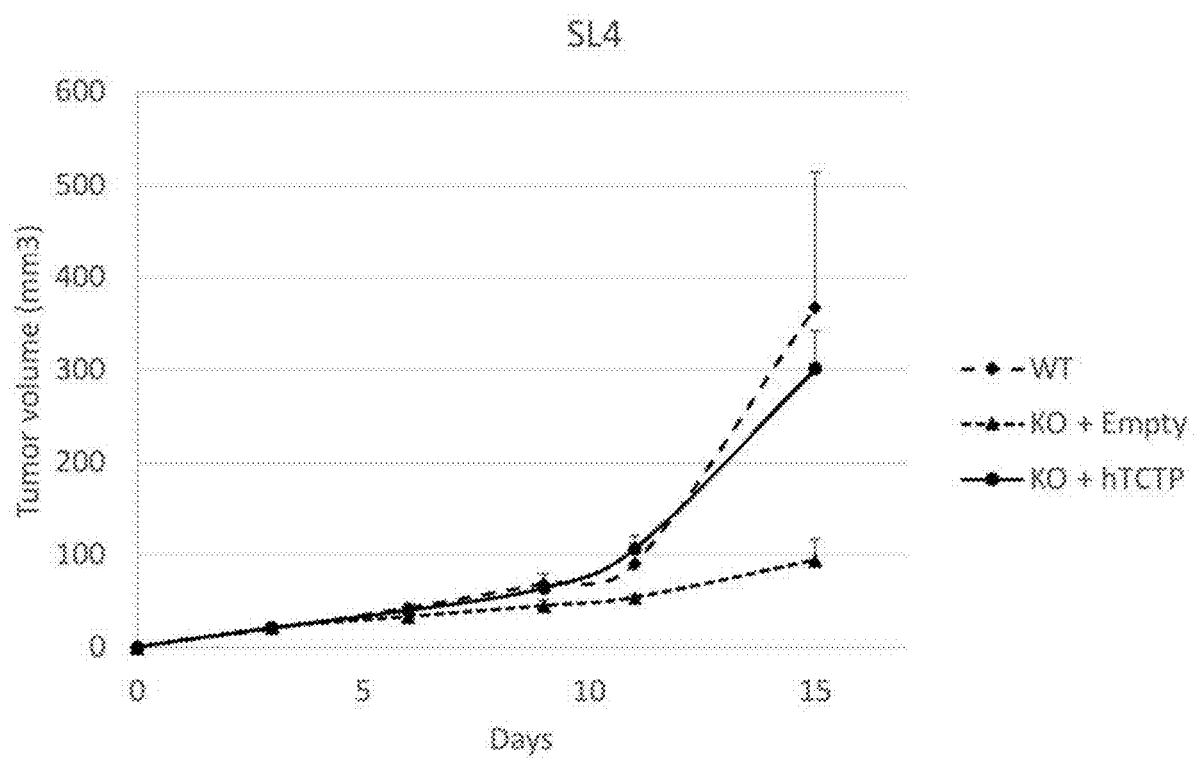
FIG. 2 shows changes in the tumor volumes of WT (wild-type), TCTP KO (knock-out), and TCTP knock-in (KO+hTCTP) SL4 cells in C57BL/6 mice over time. TCTP knock-in cells were prepared by introducing human TCTP gene into TCTP KO SL4 cells restoring TCTP expression.

As a result, as shown in FIG. 2, proliferation of a TCTP KO SL4 cell-derived tumor became significantly slow (see the plot indicated as "KO+Empty" in FIG. 2), compared with proliferation of a WT SL4 cell-derived tumor (see the plot indicated as "WT" in FIG. 2). Moreover, when a human TCTP gene was introduced again into TCTP KO SL4 cells and a human TCTP protein was allowed to express again, it was confirmed that the proliferation speed of tumors in vivo was recovered (see the plot indicated as "KO+hTCTP" in FIG. 2). Substantially the same results were obtained when carrying out the same studies using TCTP KO B16F10 cells and TCTP KO Meth-A cells. These results show that TCTP promotes tumor proliferation in vivo.

Example 4: Increased Release of TCTP from Tumor Cells

Figure 3A:
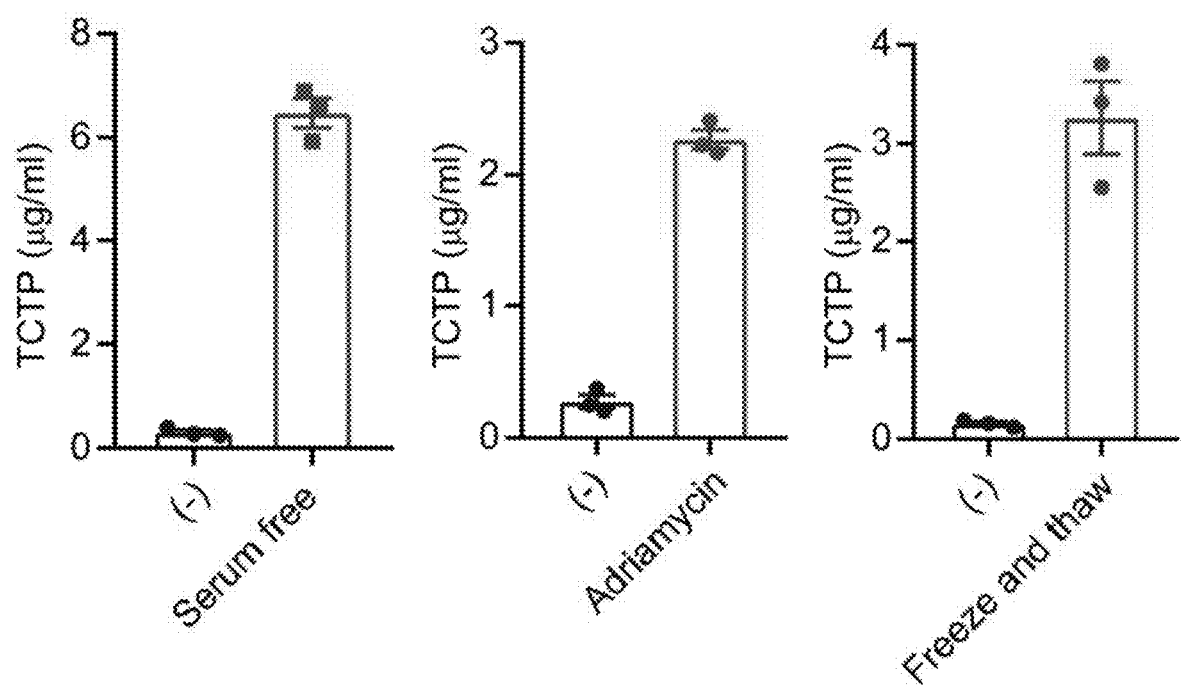
FIG. 3A. shows TCTP levels in the culture supernatant from SL4 cells that had undergone apoptosis (serum-free and adriamycin) or necrosis (freeze-and-thaw).

SL4 cells were subjected to apoptosis (serum-free and adriamycin) or necrosis (freeze-and-thaw). Conditioned media were collected and TCTP protein levels were determined by immunoblotting (n=3). As a result, TCTP was abundantly present in a culture supernatant of dead or damaged tumor cells (tumor dead cells), whereas living tumor cells (tumor living cells) hardly released TCTP (FIG. 3A).

Figure 3B:
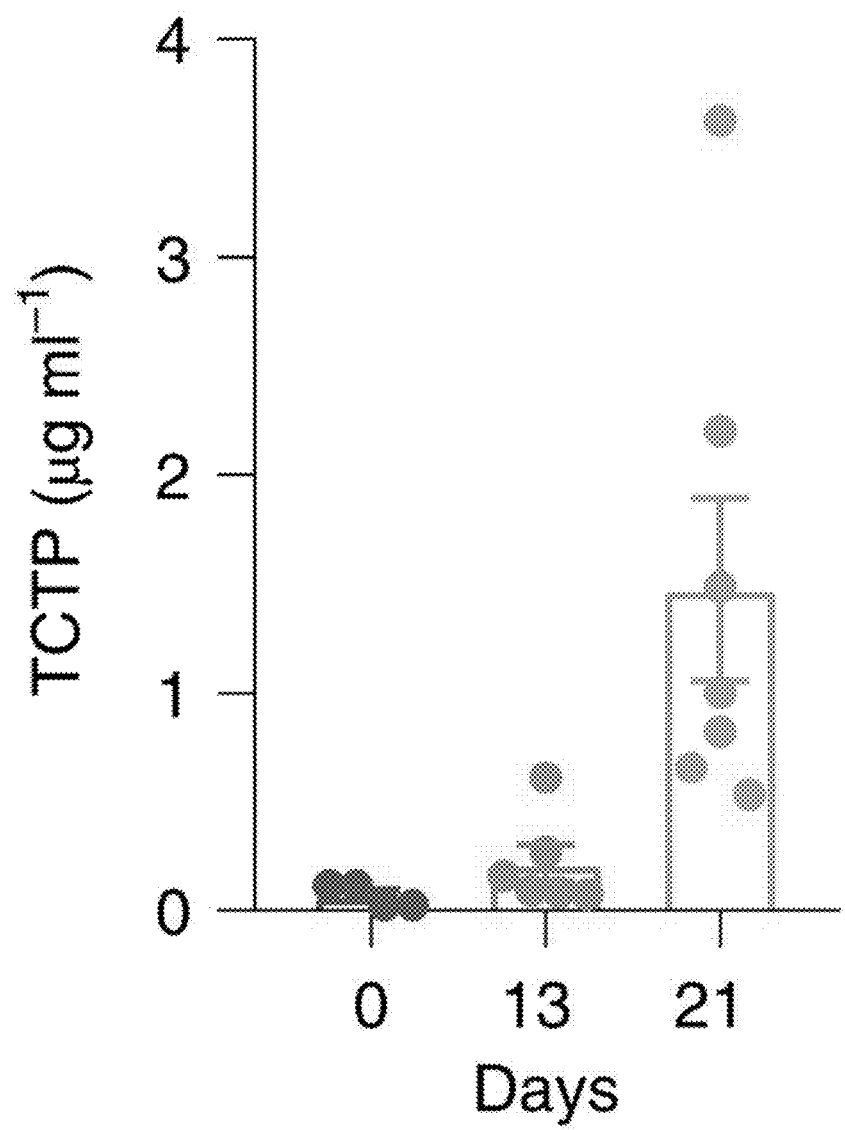
FIG. 3B. shows TCTP levels in the sera of SL4 tumor-bearing mice on Day 0 (n=4), Day 13 (n=6), and Day 21 (n=7) after subcutaneous transplantation of the tumors.

Furthermore, sera from tumor-free mice (Day 0; n=4) and SL4 tumor-bearing mice were collected on day 13 (n=6) or 21 (n=7) after subcutaneous tumor injection, and TCTP levels were quantified by immunoblotting. As shown in FIG. 3B, serum TCTP protein levels were increased over time in C57BL6 mice subcutaneously transplanted with SL4 cells.

Figure 3C:
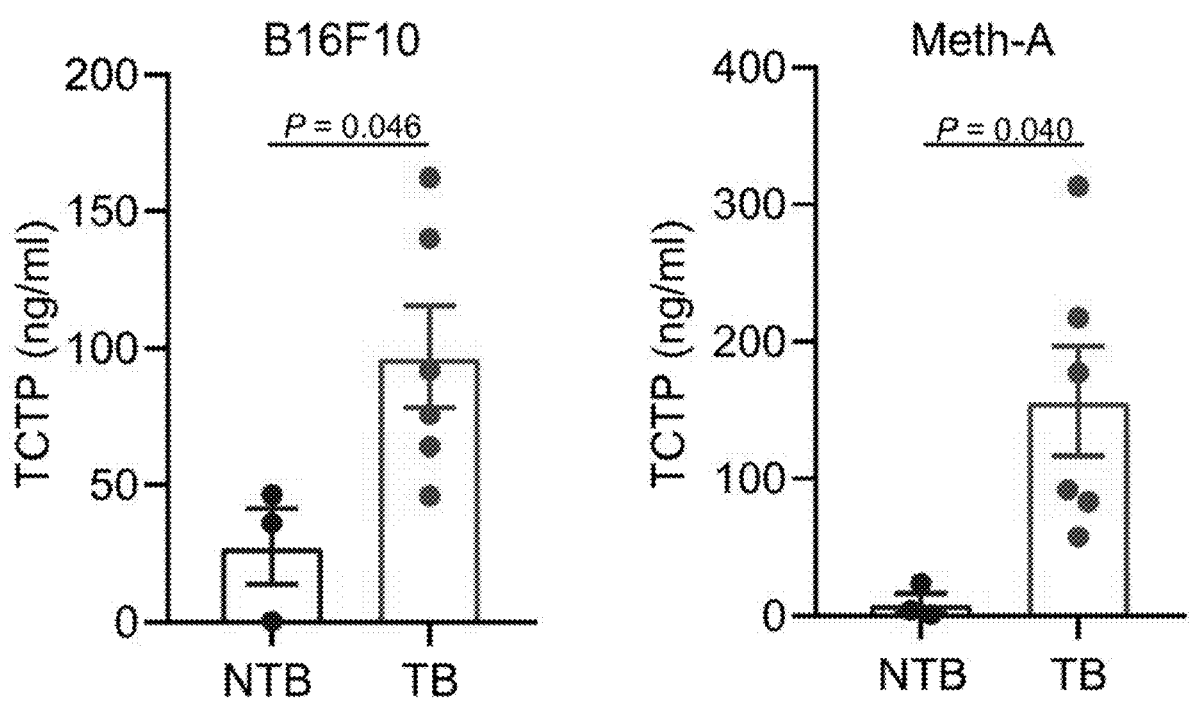
FIG. 3C. shows TCTP levels in the sera derived from mice bearing B16F10 tumor or 30 Meth-A tumor recovered on Day 0 (NTB (non-tumor bearing mice); n=3 for both groups) and Day 21 (n=5 for the B16F10 tumor group; n=6 for the Meth-A tumor group) after subcutaneous transplantation of the tumor cells.

Similar studies were conducted using B16F10 (melanoma) or Meth-A (fibrosarcoma) tumor bearing mice, and likewise, an increase in the TCTP protein levels was observed also in the sera of mice bearing B16F10 and Meth-A tumors (FIG. 3C).

These results suggested that TCTP be released from dying or damaged tumor cells in vivo.

Example 5: TCTP Released from Tumor Cells Promotes Tumor Proliferation

WT SL4 cells and TCTP KO SL4 cells ($2\times10^5$ cells) were lethally irradiated by X-ray (100 Gy) and admixed with WT cells ($2\times10^5$ cells). The obtained mixture was subcutaneously transplanted into C57BL/6 cells. Tumor volumes measured over time after subcutaneous injection.

Figure 4:
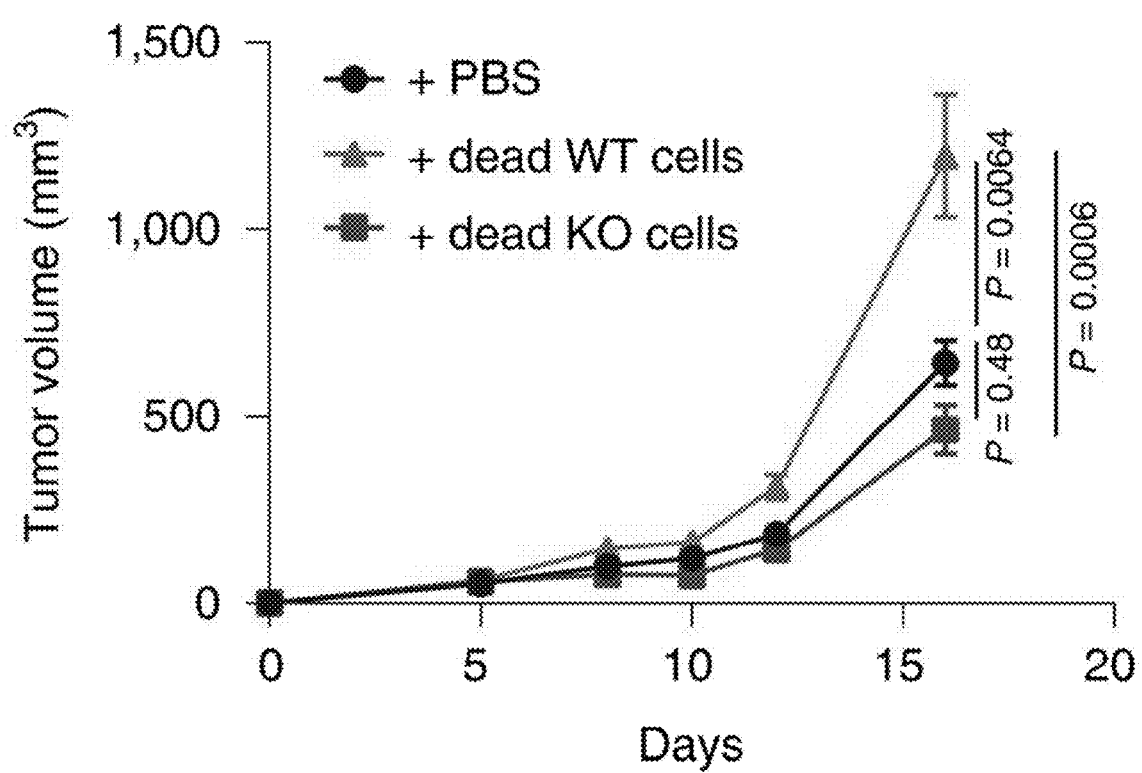
FIG. 4. shows changes in the tumor volume of SL4 cells admixed with lethally irradiated and thus dead WT cells and TCTP KO cells over time.

As a result, when WT SL4 cells (dead WT cells) irradiated with a lethal amount of X-ray were administered to mice, it promoted the growth the WT SL4 cell-derived tumor. On the other hand, when TCTP KO SL4 cells (dead KO cells) irradiated with a lethal amount of X-ray were administered to mice, it did not promote the tumor growth (FIG. 4).

This shows that dead tumor cell-derived TCTP promotes tumor suppression.

Example 6: Effect of TCTP on MDSC Accumulation

Figure 5A:
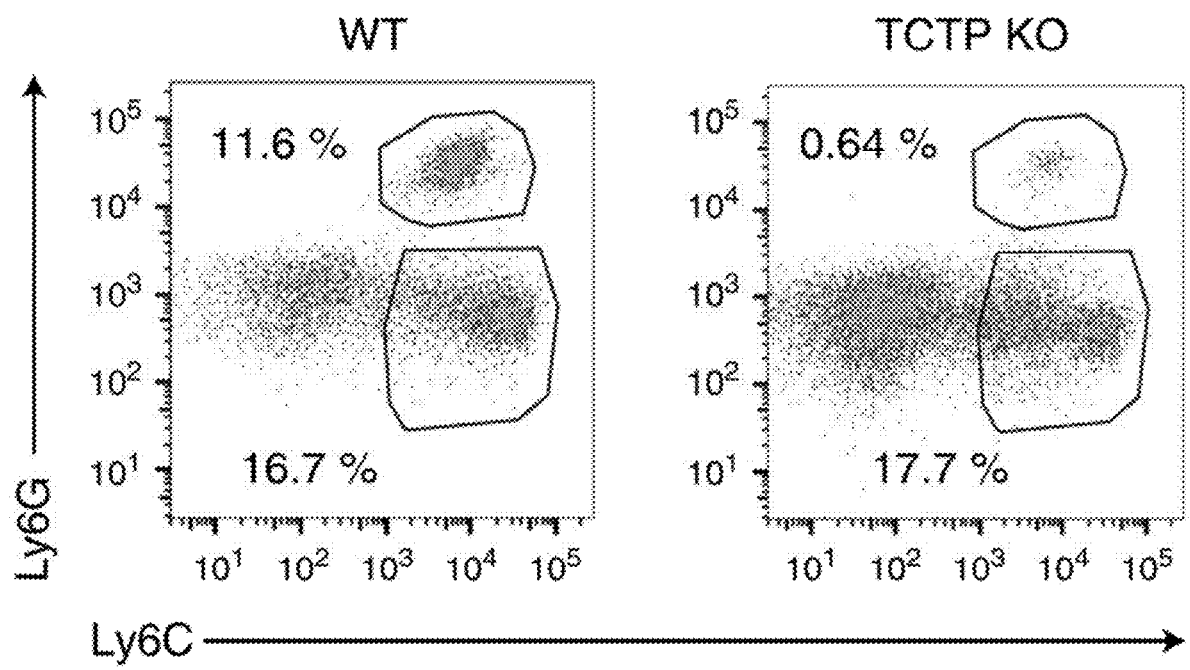
FIGS. 5A-C show flow cytometry analysis results of single cell suspensions from WT SL4 tumors and TCTP KO SL4 tumors transplanted into C57BL/6 mice (n=4). FIG. shows representative plots.
Figure 5B:
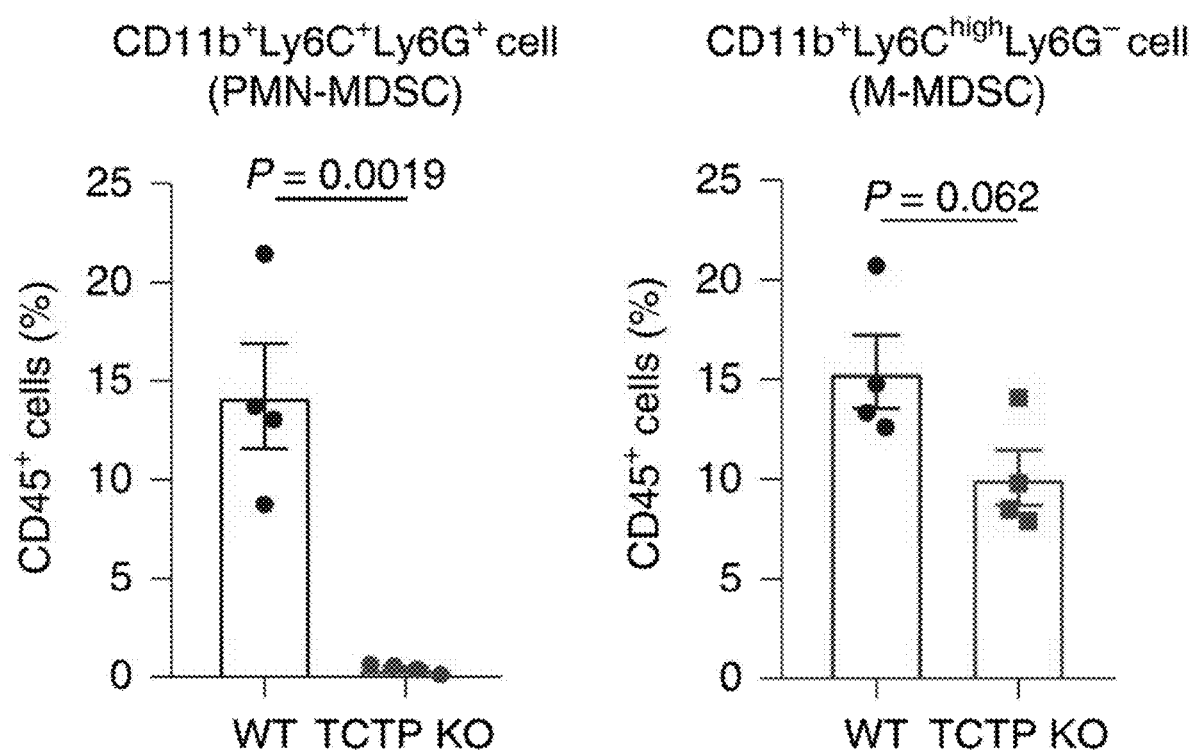
Figure 5C:
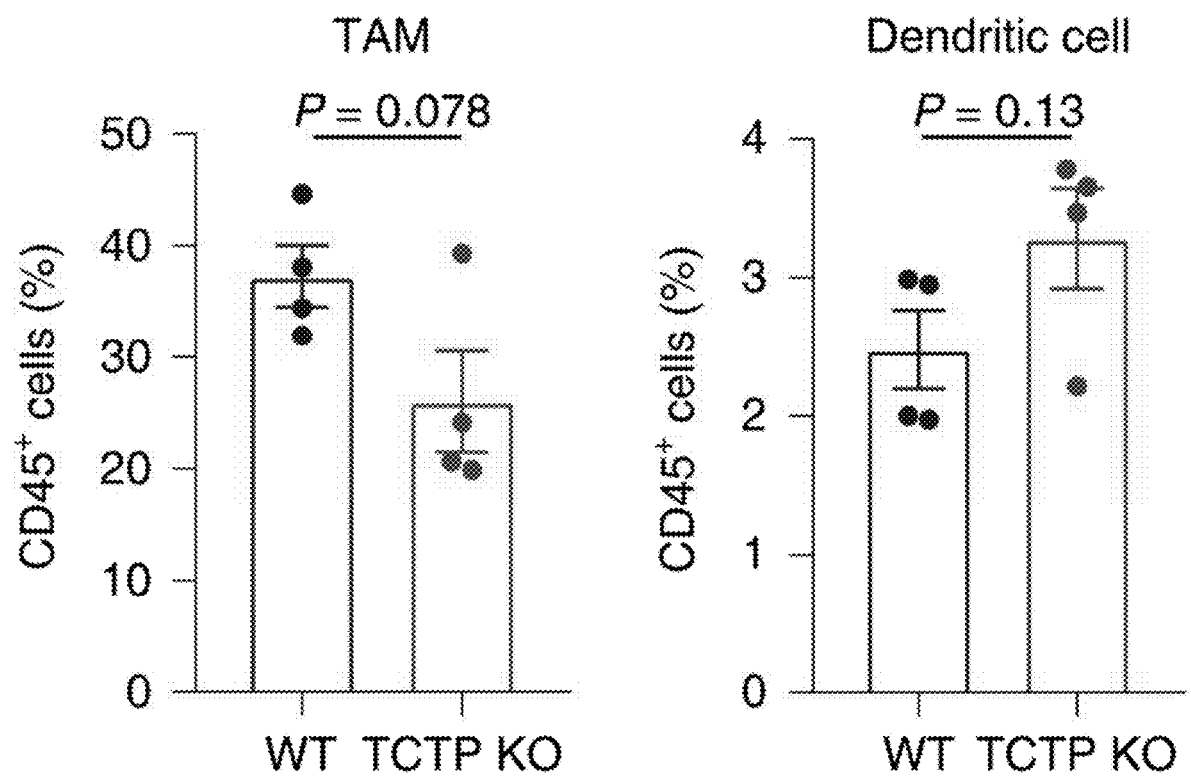

Tumor-infiltrating immune cells were prepared from WT SL4 tumors and TCTP KO SL4 tumors and were then analyzed by flow cytometry. WT and TCTP KO SL4 cells ($2\times10^5$ cells) were transplanted subcutaneously into C57BL/6 mice. After 19 days of transplantation, single cell suspensions were prepared from tumors and subjected to flow cytometry analysis (n=4). As shown in FIGS. 5A-C, it was confirmed that CD11b$^+$Ly6C$^{low}$mLy6G$^+$ cells indicating mouse PMN-MDSCs were drastically decreased in TCTP KO SL4 tumors. In contrast, CD11b$^+$Ly6Ch$^{igh}$Ly6G cells indicating M-MDSCs and bone marrow cells such as CD11b$^+$Ly6C$^-$Ly6G$^-$F4/80$^+$ tumor-associated macrophages (TAMs) did not show such drastic changes.

Figure 5D:
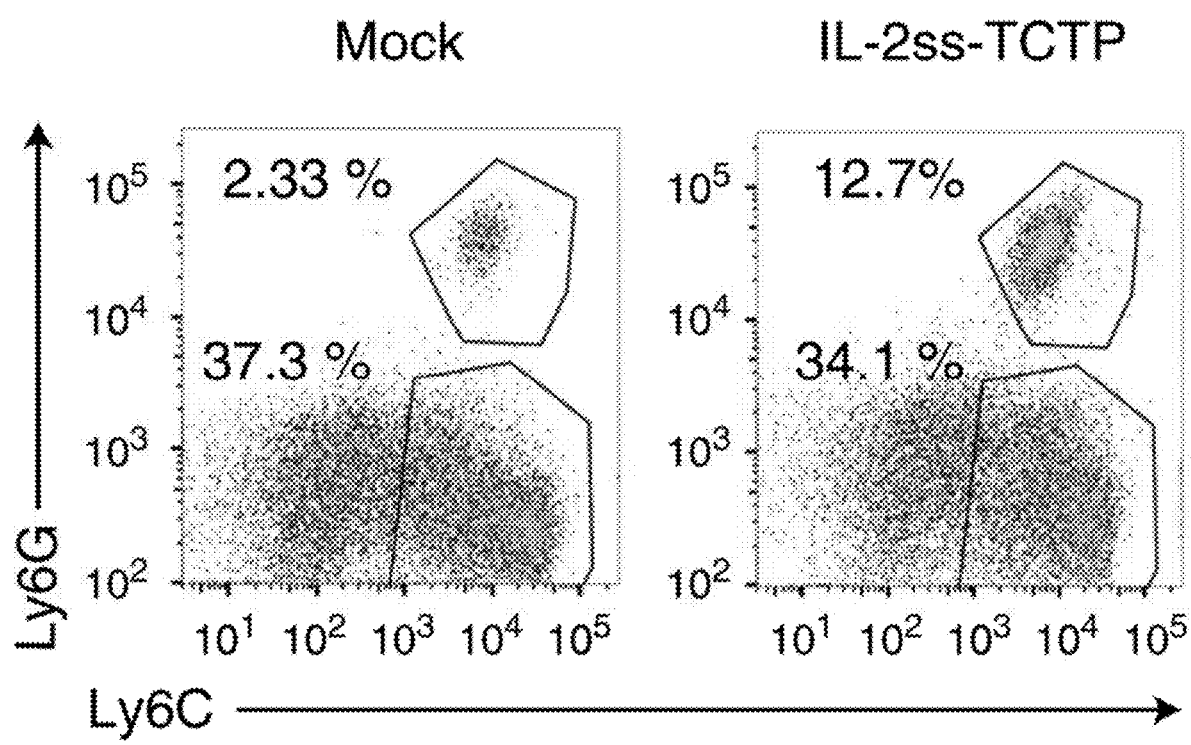
FIGS. 5D-E show flow cytometry analysis results of single cell suspensions from TCTP KO SL4 tumors (Mock) and TCTP-secreting SL4 tumors (IL-2ss-TCTP) transplanted into C57BL/6 mice (n=4).
Figure 5E:
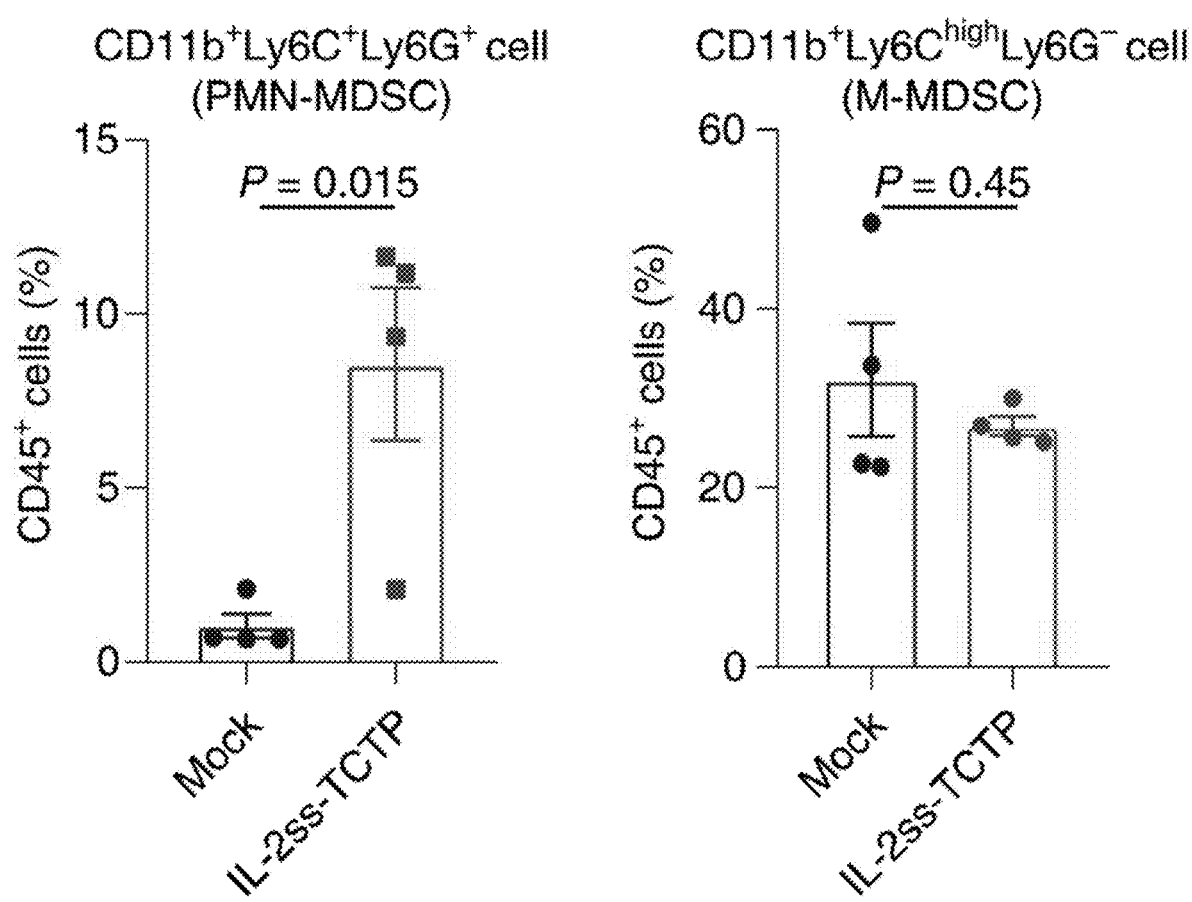

In the meantime, for extracellular secretion of TCTP, using a retroviral gene transfer vector and a protocol described in Chiba et al., Elife. 2014 Aug. 22; 3:e04177. doi: 10.7554/eLife.04177, cDNA encoding a chimeric TCTP protein with a human IL-2 signal sequence (MYRMQLLS-CIALSLALVTNS: SEQ ID NO: 37) was allowed to express in TCTP KO SL4 cells, and the resulting cells (IL-255-TCTP SL4 cells) were then allowed to proliferate in a cell medium. Mock and IL-2ss-TCTP SL4 cells ($2\times10^5$ cells) were transplanted subcutaneously into C57BL/6 mice. After 19 days of transplantation, single-cell suspensions were prepared from tumors and subject to flow cytometry analysis to determine abundances of PMN-MDSCs and M-MDSCs. As a result, the amount of PMN-MDSCs was increased in IL-2ss-TCTP tumors, compared with in TCTP KO tumors, but there was almost no difference in terms of the number of M-MDSCs (FIG. 5D-E).

These results show that extracellular TCTP promotes recruitment of MDSCs in the TIME.

Example 7: Effect of Anti-TCTP Antibody on Tumor Proliferation Suppression

Figure 6B:
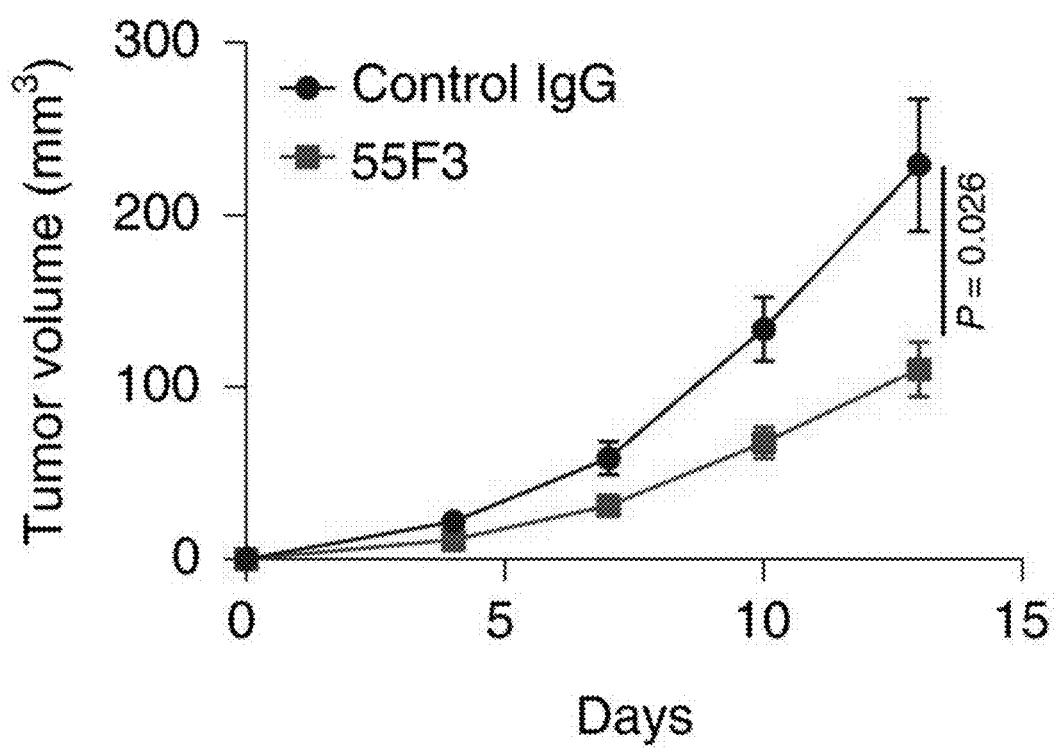
FIG. 6B shows changes in the tumor volumes of SL4 cells treated with antibody 55F3 or control IgG in C57BL/6 mice over time.

Peritoneal exudate cells (PECs) ($2\times10^5$ cells) were stimulated with conditioned supernatant of SL4 cells containing antibody 55F3 or control IgG, and after 2 hours of stimulation, Cxcl1 mRNA levels were determined by RT-qPCR. As a result of blockade of extracellular TCTP with antibody 55F3, the expression of Cxcl1 mRNA was suppressed (FIG. 6A). Subsequently, SL4 cells were transplanted into C57BL/6 mice via subcutaneous injection, and 55F3 or control IgG (200 µg/mouse) was then intraperitoneally administered to the mice every other day, starting from Day 1 after the transplantation, and the volume of the tumor was measured. As a result, the proliferation speed of SL4 tumor cells was decreased by administration of 55F3 (FIG. 6B), and the amount of PMN-MDSCs in the TIME was decreased (FIG. 6C). These results show that if the TCTP-CXCL1/2-MDSC pathway is inhibited, proliferation of tumors is suppressed.

Figure 7:
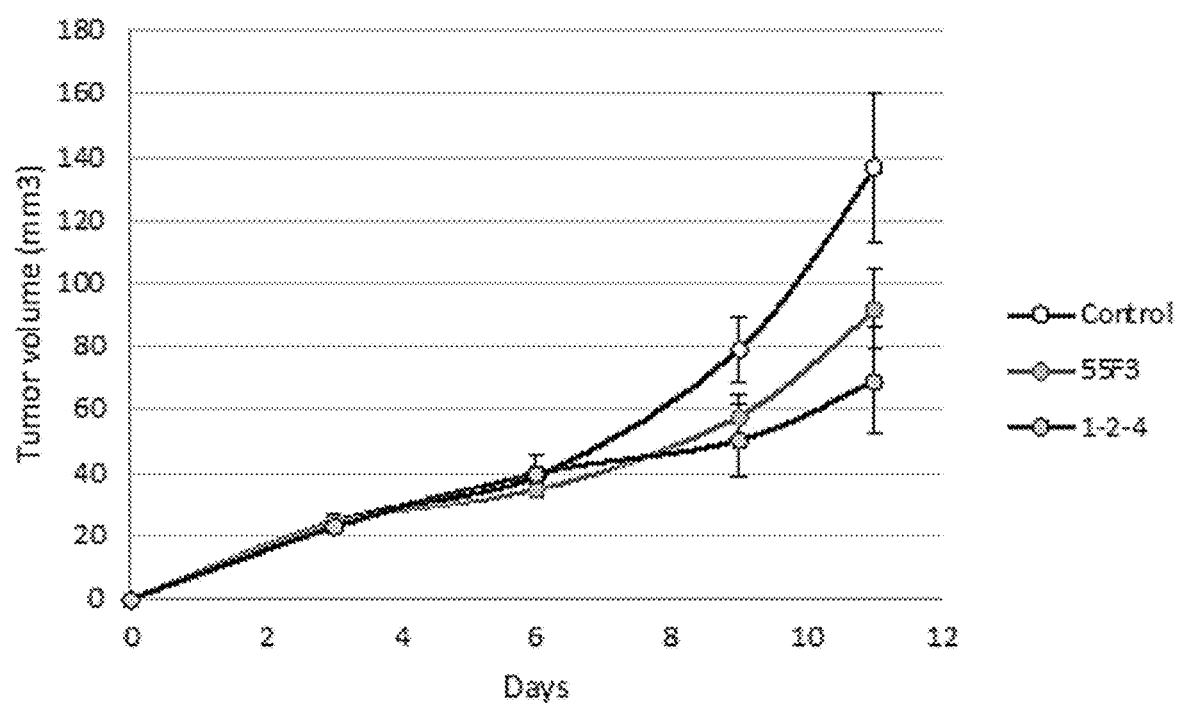
FIG. 7 shows changes in the tumor volumes of TCTP KI (knock-in) SL4 cells (from Example 3) treated with antibodies 55F3 and 1-2-4 in C57BL/6 mice over time.

TCTP KI SL4 cells (TCTP KO+hTCTP; $5\times10^5$ cells in 100 µL PBS) from example 3 were subcutaneously inoculated into C57BL/6 mice (Day 0). Anti-TCTP (100 μg in 100 μL PBS) antibodies were administered intraperitoneally into the mice on days 1, 4, 8, and 11. As a control, 100 μL of PBS was administered. Tumor size was measured on days 3, 6, 9, and 11. As a result, the proliferation speed of SL4 TCTP KO+hTCTP tumor cells was decreased by administration of 55F3 or 1-2-4 (FIG. 7).

Example 8: Effect of TCTP Inhibition in Combination with Immune Checkpoint Inhibitor on Tumor Proliferation Suppression The influence of the combination of inhibition of the function of TCTP with inhibition of various immune checkpoint inhibitors on tumor suppression was studied. As a PD-1 immune checkpoint antibody, an antibody of clone RMP1-14 (BioXCell) was used. As a PD-L1 immune checkpoint antibody, an antibody of clone 10F.9G2 (BioXCell) was used. As a CTLA-4 immune checkpoint antibody, an antibody of clone 9D9 (BioXCell) was used. SL4 WT ($2\times10^5$ cells in 100 μL PBS) and SL4 TCTP KO ($5\times10^5$ cells in 100 μL PBS) cells were subcutaneously inoculated into C57BL/6 mice (Day 0). Anti-PD-1 (100 μg in 100 μL PBS), anti-CTLA-4 (100 μg in 100 μL PBS), and anti-PD-L1 (100 μg in 100 μL PBS) antibodies were administered intraperitoneally into the mice on days 10, 14, and 17. As a control, 100 μL of PBS was administered. Tumor size was measured on days 4, 7, 10, 14, 17 and 21.

Figure 8A:
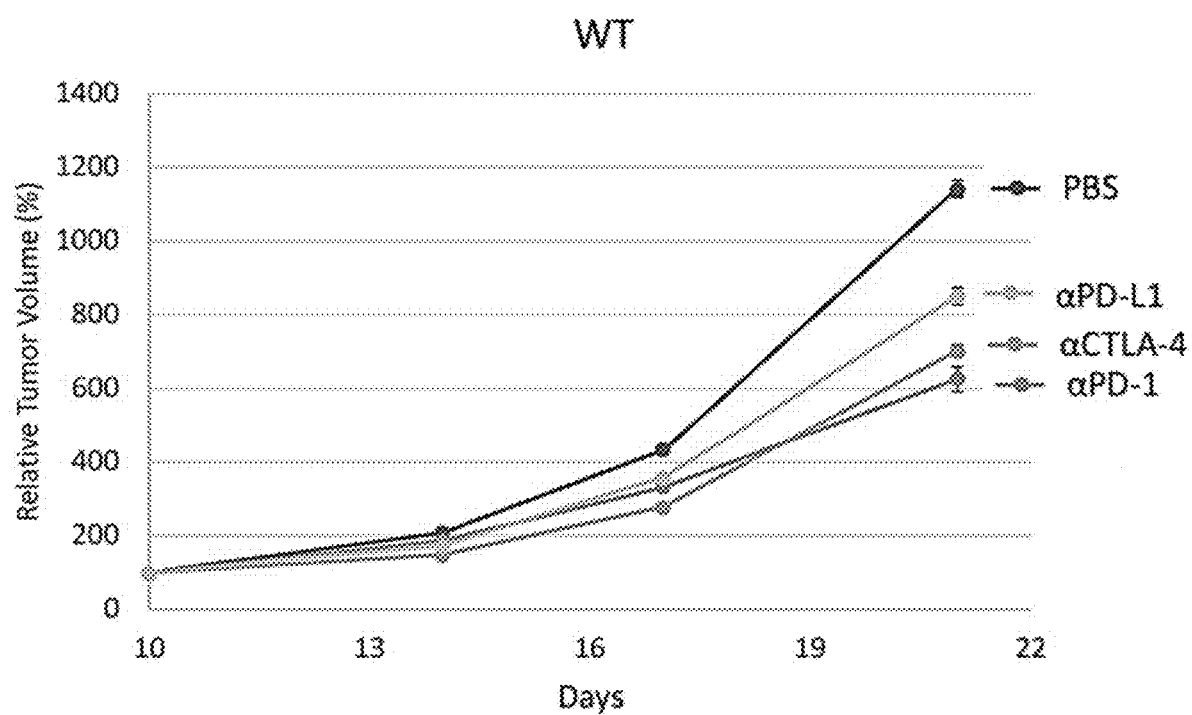
FIG. 8A shows changes in the relative tumor volumes of WT (wild-type) SL4 cells treated with anti-PD-1, anti-PD-L1, or anti-CTLA-4 antibodies. The tumor volumes were normalized to the tumor volumes at the start of the antibody treatment (Day 10).
Figure 8B:
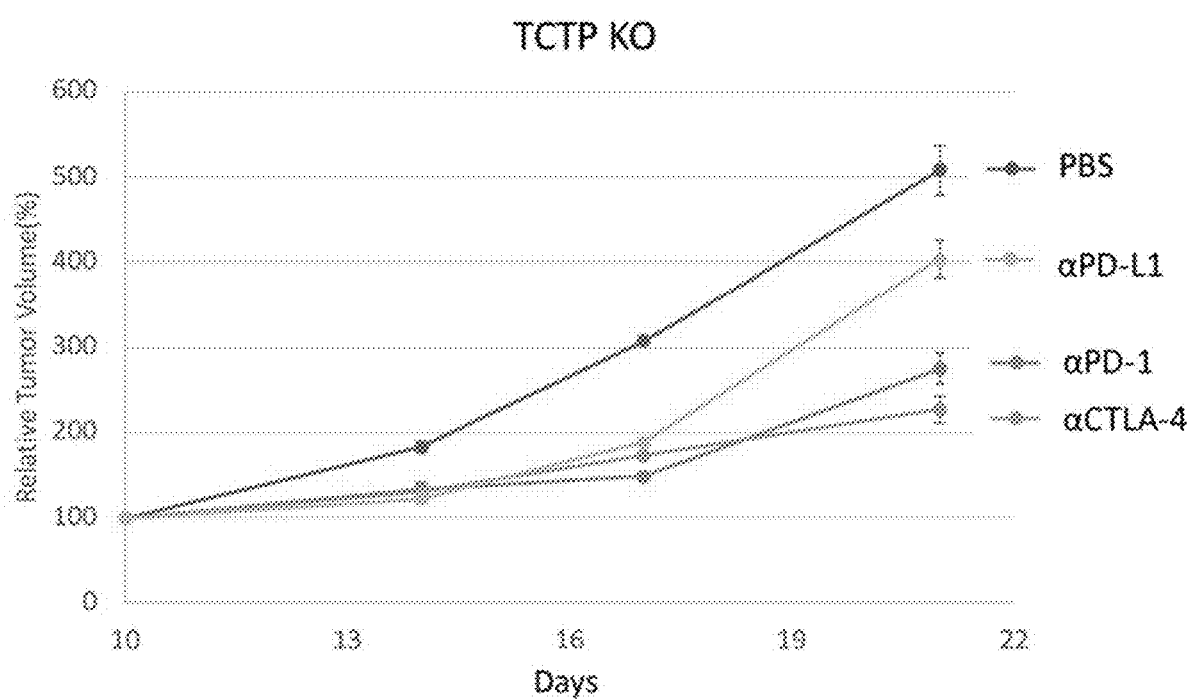
FIG. 8B shows changes in the relative tumor volumes of TCTP KO (knock-out) SL4 cells treated with anti-PD-1, anti-PD-L1, or anti-CTLA-4 antibodies. The tumor volumes were normalized to the tumor volumes at the start of the antibody treatment (Day 10).

As a result, the effect of suppressing tumor proliferation is improved by the combination of TCTP inhibition with an anti-PD-1 antibody or anti-CTLA-4 antibody. It was surprising that administration of an anti-PD1 antibody or an anti-CTLA4-antibody synergistically improved the effect of TCTP inhibition on tumor proliferation, as confirmed by the relatively more increased tumor suppression resulting from the administration of such an immune checkpoint inhibitory antibody between the WT cells and KO cells, while administration of anti-PD-L1 antibody did not exhibit such a synergistic tumor suppression effect (FIGS. 8A and 8B).

Figure 9A:
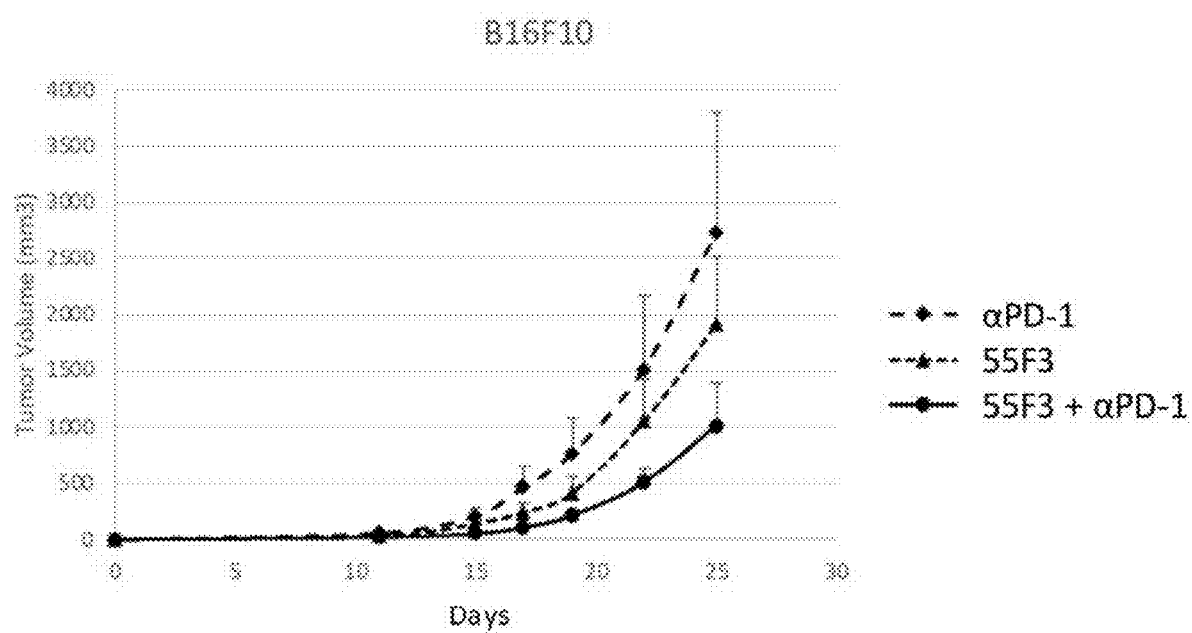
FIGS. 9A-B show changes in the tumor volumes of B16F10 cells treated with either and both of anti-PD-1 and anti-TCTP antibody 55F3 (FIG. 9A) or 1-2-4 (FIG. 9B) in C57BL/6 mice over time.
Figure 9B:
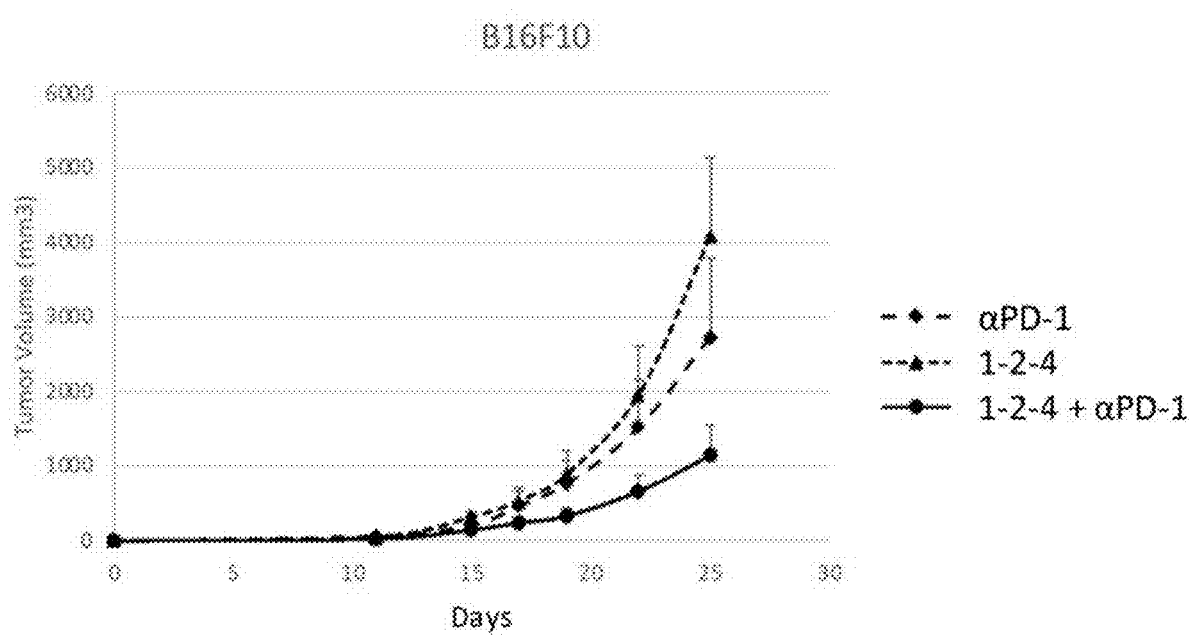

Example 9: Effect of Anti-TCTP Antibody in Combination with Anti-PD-1 Antibody on Tumor Proliferation Suppression The influence of the combination of anti-TCTP antibodies with an anti-PD-1 antibody on tumor suppression was also studied. B16F10 ($1\times10^5$ cells in 50 μL PBS) cells were subcutaneously inoculated into C57BL/6 mice (Day 1). An anti-PD-1 antibody (BioXCell; 100 μg in 100 μL PBS) was administered intravenously ten days after the inoculation, and anti-TCTP antibodies 55F3 and 1-2-4 (each 100 μg in 100 μL PBS) were administered intraperitoneally in the mice on days 1, 4, 8, 11, 15, 18, and 22. As a result, the effect of suppressing tumor proliferation is improved by the combined administration of an anti-TCTP antibody and a PD-1 or CTLA-4 antagonist antibody, compared with the case of single administration of a PD-1 or CTLA-4 antagonist antibody alone (FIGS. 9A and 9B).

Figure 10:
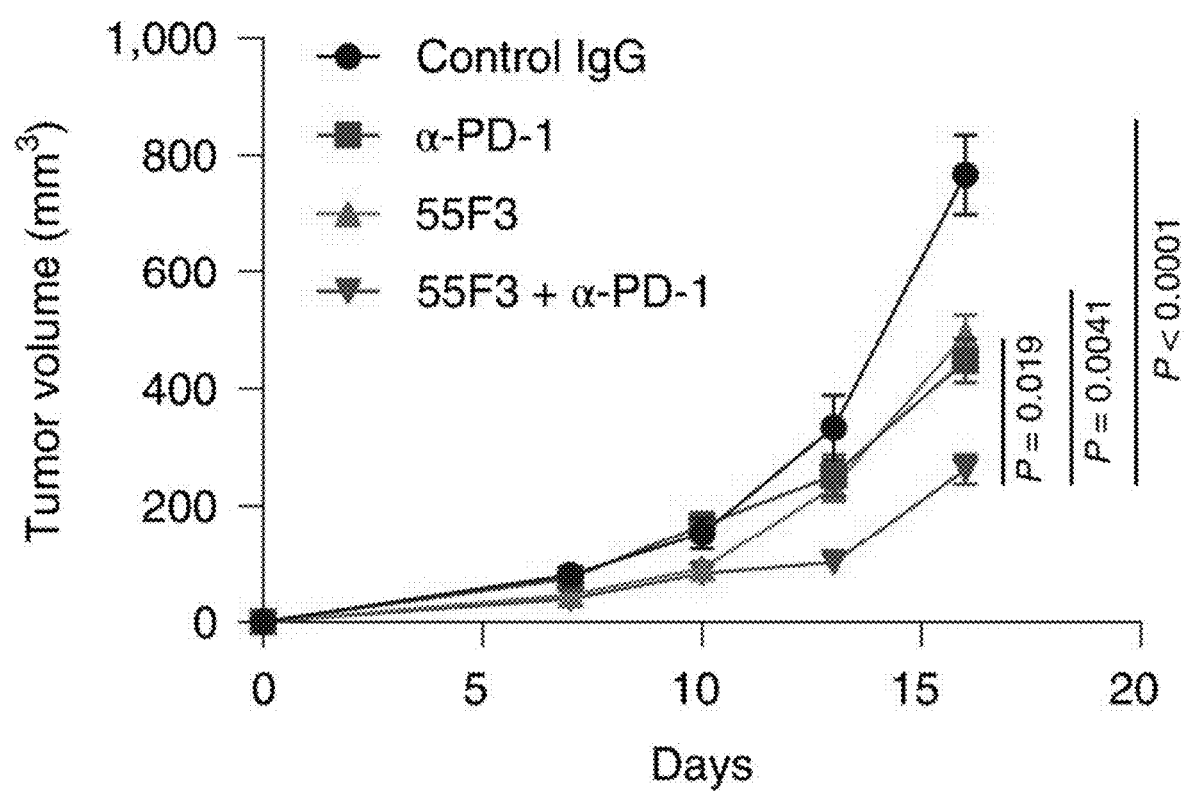
FIG. 10 shows changes in the tumor volumes of SL4 cells treated with either and both of anti-PD-1 and anti-TCTP antibody 55F3 in C57BL/6 mice over time.

This synergistic effect was also confirmed in the experiment using SL4 cells. SL4 cells were transplanted into C57BL/6 mice via subcutaneous injection, and thereafter, antibody 55F3 was intraperitoneally transplanted into the mice every day, starting from Day 1 after the transplantation. Ten days after the transplantation, an anti-PD-1 monoclonal antibody (BioLegend) was administered to the mice, and the tumor volume was then measured. As a result, it was confirmed that the effect of suppressing tumor proliferation is improved by the combined administration of an anti-TCTP antibody and a PD-1 antagonist antibody, compared with the case of single administration of a PD-1 antagonist antibody alone (FIG. 10).

Example 10: Effect of TCTP KO or Anti-TCTP Antibody on T Cells and NK Cells in TIME TCTP KO or anti-TCTP antibody alleviates the immune-suppressive environment in the TIME, which may result in activation or enhancement of anti-tumor immune cells including T cells and NK cells. The influence of the TCTP KO or anti-TCTP antibody with an anti-PD-1 antibody on T cells and NK cells in TIME was also studied.

Figure 11A:
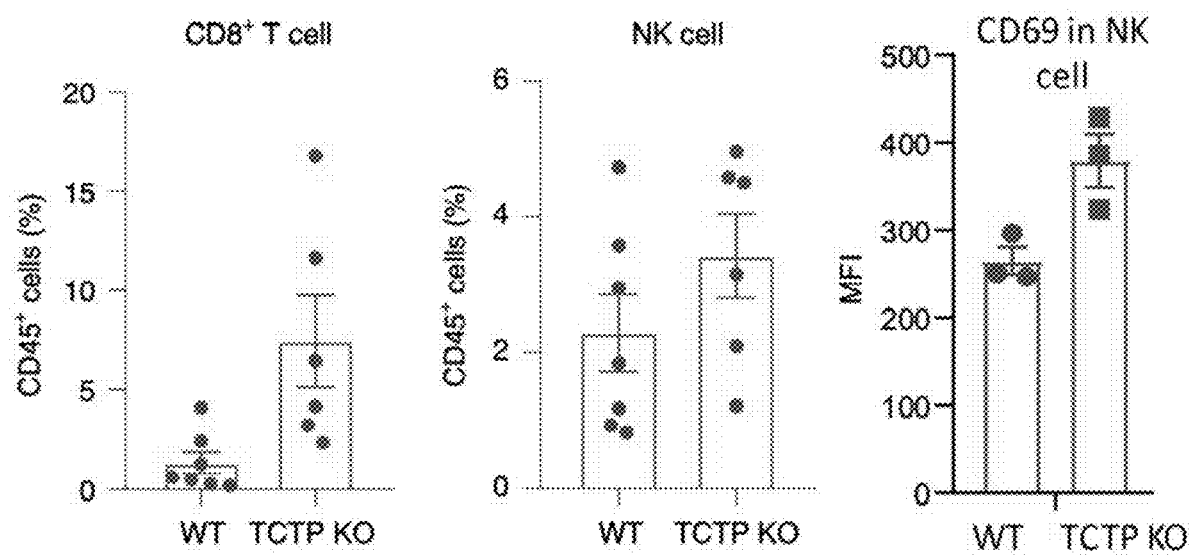
FIG. 11A shows changes in the abundance ratios or activity of CD8 T cells and NK cells from TCTP KO (knock-out) or WT (wild-type) SL4 tumors transplanted into C57BL/6 mice. MFI stands for the mean fluorescence intensity determining CD69 expression levels in NK cells.

Tumor-infiltrating immune cells were collected from WT SL4 tumors and TCTP KO SL4 tumors and were then analyzed by flow cytometry. WT and TCTP KO SL4 cells ($2\times10^5$ cells) were transplanted subcutaneously into C57BL/6 mice. After 19 days of transplantation, single cell suspensions were prepared from tumors and subjected to flow cytometry analysis. As shown in FIG. 11A, it was confirmed that CD8$^+$ T cells were increased in TCTP KO SL4 tumors. In addition, the level of the marker indicating activation of NK cells (CD69) were also elevated in TCTP KO tumor-bearing mice as compared to that from WT tumor-bearing mice.

Figure 11B:
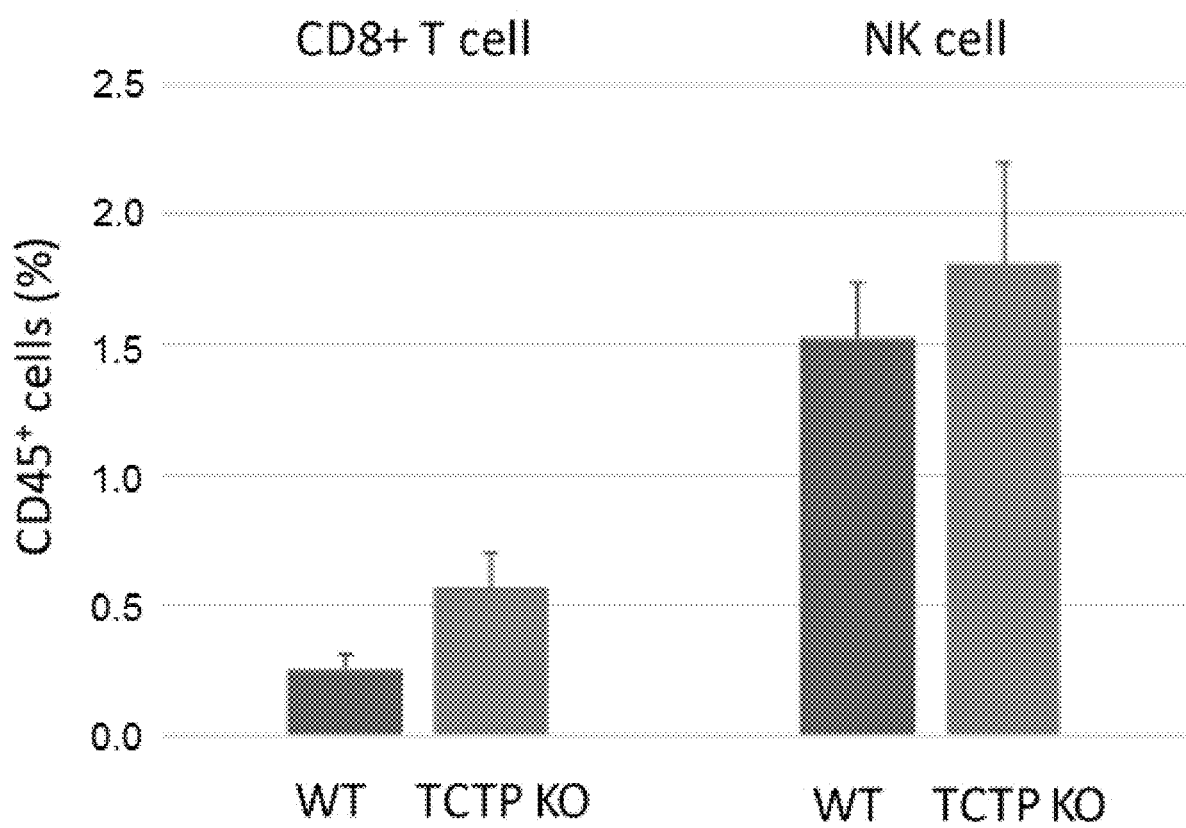
FIG. 11B shows changes in the abundance ratios of CD8+ T cells and NK cells from TCTP KO (knock-out) or WT (wild-type) B16F10 tumors transplanted into C57BL/6 mice.

Effect on T cells and NK cells in the TIME was also confirmed from the experiment using the B16F10 cell line. Tumor-infiltrating immune cells were collected from WT B16F10 tumors and TCTP KO B16F10 tumors and were then analyzed by flow cytometry. WT and TCTP KO B16F10 cells ($1\times10^5$ cells) were transplanted subcutaneously into C57BL/6 mice. After 20 days of transplantation, single cell suspensions were prepared from tumors and subjected to flow cytometry analysis. As shown in FIG. 11B, CD8$^+$ T cells and NK cells were increased in TCTP KO B16F10 tumors.

These results show that inhibition of extracellular TCTP led to the activation or enhancement of T cells and NK cells in the TIME.

Figure 11C:
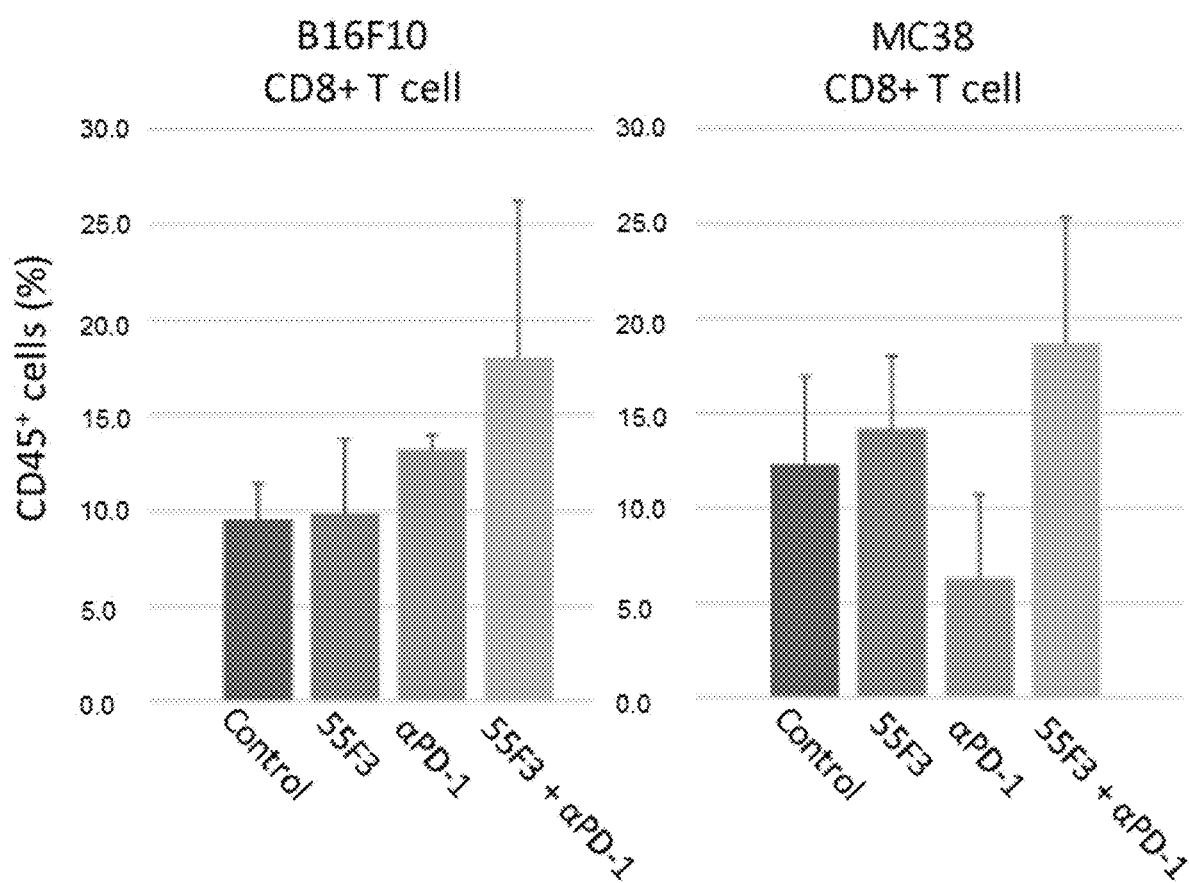
FIG. 11C shows changes in the abundance ratios of CD8+ T cells from B16F10 or MC38 tumors treated with either and both of anti-TCTP and anti-PD-1 antibodies in C57BL/6.

Effect of the combination of anti-TCTP antibody and anti-PD-1 antibody on T cells and NK cells in the TIME was also studied. Tumor-infiltrating immune cells were collected from B16F10 and MC38 tumors treated with anti-TCTP antibody and/or anti-PD-1 antibody and were then analyzed by flow cytometry. B16F10 cells ($5\times10^5$ cells) or MC38 cells ($3\times10^5$ cells) were transplanted subcutaneously into C57BL/6 mice. Anti-PD-1 antibody RMP1-14 (BioXCell; 10 mg/kg) was administered intraperitoneally on days 0, 3, 7, 10, 14 after the inoculation, and anti-TCTP antibody 55F3 (200 μg in 200 μL PBS) was administered intraperitoneally in the mice every 2 days after the inoculation. After 15 days (MC38) or 12 days (B16F10) of transplantation, single cell suspensions were prepared from tumors and subjected to flow cytometry analysis. As shown in FIG. 11C, CD8$^+$ cells were increased in both cell line groups.

These results show that the combined administration of an anti-TCTP antibody and a PD-1 antagonist antibody achieves improved activation or enhancement of tumor-killing immune cells, compared with the case of single administration of each component.

The invention claimed is:

1. A method for treating cancer in a patient in need thereof, comprising administering a combination comprising (1) a substance that suppresses or inhibits a function of extracellular translationally controlled tumor protein (TCTP) or its modified form, or a fragment or multimer thereof and (2) a cancer immunotherapeutic agent, to the patient, wherein the substance that suppresses or inhibits the function of extracellular TCTP or its modified form, or a fragment or multimer thereof is an antibody or antigen-binding fragment thereof which specifically binds to TCTP or its modified form, or a fragment or multimer thereof, and the extracellular TCTP or its modified form, or a fragment or multimer thereof has been released from tumor cells, wherein the cancer immunotherapeutic agent is an immune checkpoint inhibitor selected from an anti-PD-1 antibody and anti-CTLA-4 antibody, and wherein the antibody or antigen-binding fragment thereof, which specifically binds to TCTP or its modified form, or a fragment or multimer thereof, and the extracellular TCTP or its modified form, or a fragment or multimer thereof, comprises complementarity-determining region (CDR)-H1, CDR-H2, CDR-H3, CDR-L1, CDR-L2, and CDR-L3 selected from the group consisting of the following:

a) CDR-H1 of the sequence of SEQ ID NO: 1, CDR-H2 of the sequence of SEQ ID NO: 2, CDR-H3 of the sequence of SEQ ID NO: 3; CDR-L1 of the sequence of SEQ ID NO: 4, CDR-L2 of the sequence of SEQ ID NO: 5, and CDR-L3 of the sequence of SEQ ID NO: 6;

b) CDR-H1 of the sequence of SEQ ID NO: 7, CDR-H2 of the sequence of SEQ ID NO: 8, CDR-H3 of the sequence of SEQ ID NO: 9; CDR-L1 of the sequence of SEQ ID NO: 10, CDR-L2 of the sequence of SEQ ID NO: 11, and CDR-L3 of the sequence of SEQ ID NO: 12;

c) CDR-H1 of the sequence of SEQ ID NO: 13, CDR-H2 of the sequence of SEQ ID NO: 14, CDR-H3 of the sequence of SEQ ID NO: 15; CDR-L1 of the sequence of SEQ ID NO: 16, CDR-L2 of the sequence of SEQ ID NO: 17, and CDR-L3 of the sequence of SEQ ID NO: 18; and d) CDR-H1 of the sequence of SEQ ID NO: 19, CDR-H2 of the sequence of SEQ ID NO: 20, CDR-H3 of the sequence of SEQ ID NO: 21; CDR-L1 of the sequence of SEQ ID NO: 22, CDR-L2 of the sequence of SEQ ID NO: 23, and CDR-L3 of the sequence of SEQ ID NO: 24.

2. The method according to claim 1, wherein the cancer is selected from the group consisting of colorectal cancer, melanoma, and fibrosarcoma.

3. The method according to claim 1, wherein the substance that suppresses or inhibits the function of extracellular TCTP or its modified form, or a fragment or multimer thereof alleviates, reverts or prevents immune suppression in the tumor immune microenvironment.

4. The method according to claim 1, wherein the substance that suppresses or inhibits the function of extracellular TCTP or its modified form, or a fragment or multimer thereof activates or enhances the functions of T cells and/or NK cells.

5. The method according to claim 1, wherein the substance that suppresses or inhibits the function of extracellular TCTP or its modified form, or a fragment or multimer thereof functions as an antagonist of myeloid-derived suppressor cells (MDSCs) in the tumor immune microenvironment.

6. The method according to claim 1, wherein the patient has shown or is likely to show no or limited response to immunotherapy for the treatment of cancer.

7. The method according to claim 1, wherein (1) the substance that suppresses or inhibits the function of extracellular TCTP or a modified form, or fragment or multimer thereof and (2) the cancer immunotherapeutic agent are administered simultaneously or sequentially.

8. The method according to claim 1, wherein the substance that suppresses or inhibits the function of extracellular TCTP or its modified form, or a fragment or multimer thereof, competitively inhibits binding of an anti-TCTP antibody to TCTP, wherein said anti-TCTP antibody comprises CDR-H1, CDR-H2, CDR-H3, CDR-L1, CDR-L2, and CDR-L3 selected from the group consisting of the following:

a) CDR-H1 of the sequence of SEQ ID NO: 1, CDR-H2 of the sequence of SEQ ID NO: 2, CDR-H3 of the sequence of SEQ ID NO: 3; CDR-L1 of the sequence of SEQ ID NO: 4, CDR-L2 of the sequence of SEQ ID NO: 5, and CDR-L3 of the sequence of SEQ ID NO: 6;

b) CDR-H1 of the sequence of SEQ ID NO: 7, CDR-H2 of the sequence of SEQ ID NO: 8, CDR-H3 of the sequence of SEQ ID NO: 9; CDR-L1 of the sequence of SEQ ID NO: 10, CDR-L2 of the sequence of SEQ ID NO: 11, and CDR-L3 of the sequence of SEQ ID NO: 12;

c) CDR-H1 of the sequence of SEQ ID NO: 13, CDR-H2 of the sequence of SEQ ID NO: 14, CDR-H3 of the sequence of SEQ ID NO: 15; CDR-L3 of the sequence of SEQ ID NO: 16, CDR-L2 of the sequence of SEQ ID NO: 17, and CDR-L3 of the sequence of SEQ ID NO: 18; and d) CDR-H1 of the sequence of SEQ ID NO: 19, CDR-H2 of the sequence of SEQ ID NO: 20, CDR-H3 of the sequence of SEQ ID NO: 21; CDR-L1 of the sequence of SEQ ID NO: 22, CDR-L2 of the sequence of SEQ ID NO: 23, and CDR-L3 of the sequence of SEQ ID NO: 24.

* * * * *

SEQUENCE LISTING

```
<160> NUMBER OF SEQ ID NOS: 37

<210> SEQ ID NO 1
<211> LENGTH: 11
<212> TYPE: PRT
<213> ORGANISM: Mus musculus

<400> SEQUENCE: 1

Gly Tyr Ser Ile Ala Ser Asp Tyr Ala Trp Asn
1               5                   10

<210> SEQ ID NO 2
<211> LENGTH: 16
<212> TYPE: PRT
<213> ORGANISM: Mus musculus

<400> SEQUENCE: 2

Tyr Ile Asn Tyr Ser Gly Ser Thr Gly Tyr Asn Pro Ser Leu Lys Ser
1               5                   10                  15

<210> SEQ ID NO 3
<211> LENGTH: 5
<212> TYPE: PRT
<213> ORGANISM: Mus musculus

<400> SEQUENCE: 3

Phe Glu Ala Gly Tyr
1               5

<210> SEQ ID NO 4
<211> LENGTH: 11
<212> TYPE: PRT
<213> ORGANISM: Mus musculus

<400> SEQUENCE: 4

Lys Ala Ser Gln Asp Ile Asn Arg Tyr Leu Ser
1               5                   10

<210> SEQ ID NO 5
<211> LENGTH: 7
<212> TYPE: PRT
<213> ORGANISM: Mus musculus

<400> SEQUENCE: 5

Arg Ala Asn Arg Leu Val Asp
1               5

<210> SEQ ID NO 6
<211> LENGTH: 9
<212> TYPE: PRT
<213> ORGANISM: Mus musculus

<400> SEQUENCE: 6

Leu Gln Tyr Asn Glu Phe Pro Leu Thr
1               5

<210> SEQ ID NO 7
<211> LENGTH: 10
<212> TYPE: PRT
<213> ORGANISM: Mus musculus

<400> SEQUENCE: 7

Gly Tyr Thr Phe Thr Asp His Ala Ile His
1               5                   10
```

<210> SEQ ID NO 8
<211> LENGTH: 17
<212> TYPE: PRT
<213> ORGANISM: Mus musculus

<400> SEQUENCE: 8

Tyr Ile Ser Pro Gly Asn Gly Asp Leu Lys Tyr Asn Glu Lys Phe Lys
1               5                   10                  15

Gly

<210> SEQ ID NO 9
<211> LENGTH: 4
<212> TYPE: PRT
<213> ORGANISM: Mus musculus

<400> SEQUENCE: 9

Gly Trp Thr Leu
1

<210> SEQ ID NO 10
<211> LENGTH: 17
<212> TYPE: PRT
<213> ORGANISM: Mus musculus

<400> SEQUENCE: 10

Lys Ser Ser Gln Ser Leu Leu Tyr Arg Ser Asn Gln Lys Asn Tyr Leu
1               5                   10                  15

Val

<210> SEQ ID NO 11
<211> LENGTH: 7
<212> TYPE: PRT
<213> ORGANISM: Mus musculus

<400> SEQUENCE: 11

Trp Ala Phe Thr Arg Glu Ser
1               5

<210> SEQ ID NO 12
<211> LENGTH: 9
<212> TYPE: PRT
<213> ORGANISM: Mus musculus

<400> SEQUENCE: 12

Gln Gln His Tyr Ser Tyr Pro Trp Thr
1               5

<210> SEQ ID NO 13
<211> LENGTH: 11
<212> TYPE: PRT
<213> ORGANISM: Mus musculus

<400> SEQUENCE: 13

Gly Tyr Ser Ile Thr Ser Asp Tyr Ala Trp Asn
1               5                   10

<210> SEQ ID NO 14
<211> LENGTH: 16
<212> TYPE: PRT
<213> ORGANISM: Mus musculus

<400> SEQUENCE: 14

Tyr Ile Asn Tyr Ser Gly Ser Thr Gly Tyr Asn Pro Ser Leu Lys Ser

```
<210> SEQ ID NO 15
<211> LENGTH: 5
<212> TYPE: PRT
<213> ORGANISM: Mus musculus

<400> SEQUENCE: 15

Phe Glu Ala Gly Tyr
1               5

<210> SEQ ID NO 16
<211> LENGTH: 11
<212> TYPE: PRT
<213> ORGANISM: Mus musculus

<400> SEQUENCE: 16

Lys Ala Ser Gln Asp Ile Asn Ser Tyr Leu Ser
1               5                   10

<210> SEQ ID NO 17
<211> LENGTH: 7
<212> TYPE: PRT
<213> ORGANISM: Mus musculus

<400> SEQUENCE: 17

Arg Ala Asn Arg Leu Val Asp
1               5

<210> SEQ ID NO 18
<211> LENGTH: 9
<212> TYPE: PRT
<213> ORGANISM: Mus musculus

<400> SEQUENCE: 18

Leu Gln Tyr Tyr Glu Phe Pro Leu Thr
1               5

<210> SEQ ID NO 19
<211> LENGTH: 5
<212> TYPE: PRT
<213> ORGANISM: Artificial Sequence
<220> FEATURE:
<223> OTHER INFORMATION: CDR1

<400> SEQUENCE: 19

Ser Tyr Ala Met His
1               5

<210> SEQ ID NO 20
<211> LENGTH: 17
<212> TYPE: PRT
<213> ORGANISM: Artificial Sequence
<220> FEATURE:
<223> OTHER INFORMATION: CDR2

<400> SEQUENCE: 20

Trp Ile Asn Ala Gly Asn Gly Asn Thr Lys Tyr Ser Gln Lys Phe Gln
1               5                   10                  15

Asp

<210> SEQ ID NO 21
<211> LENGTH: 5
<212> TYPE: PRT
<213> ORGANISM: Artificial Sequence
```

```
<220> FEATURE:
<223> OTHER INFORMATION: CDR3

<400> SEQUENCE: 21

Trp Val Phe Asp Tyr
1               5

<210> SEQ ID NO 22
<211> LENGTH: 16
<212> TYPE: PRT
<213> ORGANISM: Artificial Sequence
<220> FEATURE:
<223> OTHER INFORMATION: CDR1

<400> SEQUENCE: 22

Arg Ser Ser Gln Ser Leu Val His Arg Asp Gly Asn Thr Tyr Leu Ser
1               5                  10                  15

<210> SEQ ID NO 23
<211> LENGTH: 7
<212> TYPE: PRT
<213> ORGANISM: Artificial Sequence
<220> FEATURE:
<223> OTHER INFORMATION: CDR2

<400> SEQUENCE: 23

Lys Ile Ser Asn Arg Phe Phe
1               5

<210> SEQ ID NO 24
<211> LENGTH: 9
<212> TYPE: PRT
<213> ORGANISM: Artificial Sequence
<220> FEATURE:
<223> OTHER INFORMATION: CDR3

<400> SEQUENCE: 24

Met Gln Ala Thr Gln Phe Pro His Thr
1               5

<210> SEQ ID NO 25
<211> LENGTH: 170
<212> TYPE: PRT
<213> ORGANISM: Mus musculus

<400> SEQUENCE: 25

Met Arg Val Leu Ile Leu Leu Trp Leu Phe Thr Ala Phe Pro Gly Ile
1               5                   10                  15

Leu Ser Asp Val Gln Leu Gln Glu Ser Gly Pro Gly Leu Val Lys Pro
                20                  25                  30

Ser Gln Ser Leu Ser Leu Thr Cys Thr Ala Thr Gly Tyr Ser Ile Ala
            35                  40                  45

Ser Asp Tyr Ala Trp Asn Trp Ile Arg Gln Phe Pro Gly Asn Lys Leu
        50                  55                  60

Glu Trp Met Gly Tyr Ile Asn Tyr Ser Gly Ser Thr Gly Tyr Asn Pro
65                  70                  75                  80

Ser Leu Lys Ser Arg Ile Ser Ile Thr Arg Asp Thr Ser Lys Asn Gln
                85                  90                  95

Phe Phe Leu Gln Leu Asn Ser Val Thr Thr Glu Asp Thr Ala Thr Tyr
            100                 105                 110

Tyr Cys Ala Arg Phe Glu Ala Gly Tyr Trp Gly Gln Gly Thr Thr Leu
        115                 120                 125
```

```
Thr Val Ser Ser Ala Lys Thr Thr Pro Pro Ser Val Tyr Pro Leu Ala
            130                 135                 140
Pro Gly Ser Ala Ala Gln Thr Asn Ser Met Val Thr Leu Gly Cys Leu
145                 150                 155                 160
Val Lys Gly Tyr Phe Pro Glu Pro Val Thr
                165                 170

<210> SEQ ID NO 26
<211> LENGTH: 170
<212> TYPE: PRT
<213> ORGANISM: Mus musculus

<400> SEQUENCE: 26

Met Glu Trp Ser Trp Val Phe Leu Phe Phe Leu Ser Val Thr Thr Gly
1               5                   10                  15
Val His Ser Glu Val Gln Leu Gln Gln Ser Asp Ala Glu Leu Val Lys
            20                  25                  30
Pro Gly Ala Ser Val Lys Ile Ser Cys Lys Ala Ser Gly Tyr Thr Phe
        35                  40                  45
Thr Asp His Ala Ile His Trp Ala Lys Gln Lys Pro Glu Gln Gly Leu
    50                  55                  60
Glu Trp Ile Gly Tyr Ile Ser Pro Gly Asn Gly Asp Leu Lys Tyr Asn
65                  70                  75                  80
Glu Lys Phe Lys Gly Lys Ala Thr Leu Thr Thr Asp Lys Ser Ser Ser
                85                  90                  95
Thr Ala Tyr Met Gln Leu Asn Ser Leu Thr Ser Glu Asp Ser Ala Val
            100                 105                 110
Tyr Phe Cys Lys Ser Gly Trp Thr Leu Trp Gly Gln Gly Thr Thr Leu
        115                 120                 125
Thr Val Ser Ser Ala Lys Thr Thr Pro Pro Ser Val Tyr Pro Leu Ala
    130                 135                 140
Pro Gly Ser Ala Ala Gln Thr Asn Ser Met Val Thr Leu Gly Cys Leu
145                 150                 155                 160
Val Lys Gly Tyr Phe Pro Glu Pro Val Thr
                165                 170

<210> SEQ ID NO 27
<211> LENGTH: 170
<212> TYPE: PRT
<213> ORGANISM: Mus musculus

<400> SEQUENCE: 27

Met Arg Val Leu Ile Leu Leu Trp Leu Phe Thr Ala Phe Pro Gly Ile
1               5                   10                  15
Leu Ser Asp Val Gln Leu Gln Glu Ser Gly Pro Gly Leu Val Lys Pro
            20                  25                  30
Ser Gln Ser Leu Ser Leu Thr Cys Thr Ala Thr Gly Tyr Ser Ile Thr
        35                  40                  45
Ser Asp Tyr Ala Trp Asn Trp Ile Arg Gln Phe Pro Gly Asn Lys Leu
    50                  55                  60
Glu Trp Met Gly Tyr Ile Asn Tyr Ser Gly Ser Thr Gly Tyr Asn Pro
65                  70                  75                  80
Ser Leu Lys Ser Arg Ile Ser Ile Thr Arg Asp Thr Ser Lys Asn Lys
                85                  90                  95
Phe Phe Leu Gln Leu Asn Ser Val Thr Thr Glu Asp Thr Ala Thr Tyr
            100                 105                 110
```

```
Tyr Cys Ala Arg Phe Glu Ala Gly Tyr Trp Gly Gln Gly Thr Thr Leu
            115                 120                 125

Thr Val Ser Ser Ala Lys Thr Thr Pro Pro Ser Val Tyr Pro Leu Ala
    130                 135                 140

Pro Gly Ser Ala Ala Gln Thr Asn Ser Met Val Thr Leu Gly Cys Leu
145                 150                 155                 160

Val Lys Gly Tyr Phe Pro Glu Pro Val Thr
                165                 170

<210> SEQ ID NO 28
<211> LENGTH: 133
<212> TYPE: PRT
<213> ORGANISM: Artificial Sequence
<220> FEATURE:
<223> OTHER INFORMATION: Variable region of antibody

<400> SEQUENCE: 28

Met Asp Trp Thr Trp Arg Ile Leu Phe Leu Val Ala Ala Ala Thr Gly
1               5                   10                  15

Ala His Ser Gln Val Gln Leu Val Gln Ser Gly Ala Glu Val Lys Lys
            20                  25                  30

Pro Gly Ala Ser Val Lys Val Ser Cys Lys Ala Ser Gly Tyr Thr Phe
        35                  40                  45

Phe Ser Tyr Ala Met His Trp Val Arg Gln Ala Pro Gly Gln Arg Leu
    50                  55                  60

Glu Trp Met Gly Trp Ile Asn Ala Gly Asn Gly Asn Thr Lys Tyr Ser
65              70                  75                  80

Gln Lys Phe Gln Asp Arg Val Thr Ile Thr Arg Asp Thr Ser Ala Thr
            85                  90                  95

Thr Ala Tyr Met Glu Leu Ser Ser Leu Arg Ser Glu Asp Thr Ala Val
            100                 105                 110

Tyr Tyr Cys Ala Ser Trp Val Phe Asp Tyr Trp Gly Gln Gly Thr Pro
        115                 120                 125

Val Thr Val Ser Ser
    130

<210> SEQ ID NO 29
<211> LENGTH: 159
<212> TYPE: PRT
<213> ORGANISM: Mus musculus

<400> SEQUENCE: 29

Met Asp Met Arg Thr Pro Ala Gln Phe Leu Gly Ile Leu Leu Leu Trp
1               5                   10                  15

Phe Pro Gly Ile Lys Cys Asp Ile Lys Met Thr Gln Ser Pro Ser Ser
            20                  25                  30

Met Ser Ala Ser Leu Gly Glu Arg Val Thr Ile Thr Cys Lys Ala Ser
        35                  40                  45

Gln Asp Ile Asn Arg Tyr Leu Ser Trp Phe Gln Lys Pro Gly Lys Ser
    50                  55                  60

Pro Lys Thr Leu Ile Tyr Arg Ala Asn Arg Leu Val Asp Gly Val Pro
65              70                  75                  80

Ser Arg Phe Ser Gly Ser Gly Ser Gly Gln Asp Tyr Ser Leu Thr Ile
            85                  90                  95

Ser Ser Leu Glu Tyr Gly Asp Met Gly Ile Tyr Tyr Cys Leu Gln Tyr
            100                 105                 110

Asn Glu Phe Pro Leu Thr Phe Gly Ala Gly Thr Lys Leu Glu Leu
```

```
            115                 120                 125
Lys Arg Ala Asp Ala Ala Pro Thr Val Ser Ile Phe Pro Ser Ser
            130                 135                 140

Glu Gln Leu Thr Ser Gly Gly Ala Ser Val Val Cys Phe Leu Asn
145                 150                 155
```

<210> SEQ ID NO 30
<211> LENGTH: 163
<212> TYPE: PRT
<213> ORGANISM: Mus musculus

<400> SEQUENCE: 30

```
Met Asp Ser Gln Ala Gln Val Leu Met Leu Leu Leu Trp Val Ser
1               5                   10                  15

Gly Thr Cys Gly Asp Ile Val Met Ser Gln Ser Pro Ser Ser Pro Val
                20                  25                  30

Val Ser Val Gly Glu Lys Val Thr Met Ser Cys Lys Ser Ser Gln Ser
                35                  40                  45

Leu Leu Tyr Arg Ser Asn Gln Lys Asn Tyr Leu Val Trp Tyr Gln Leu
            50                  55                  60

Lys Pro Gly Gln Ser Pro Lys Leu Leu Ile Tyr Trp Ala Phe Thr Arg
65                  70                  75                  80

Glu Ser Gly Val Pro Asp Arg Phe Thr Gly Ser Gly Ser Gly Thr Asp
                85                  90                  95

Phe Thr Leu Thr Ile Ser Ser Val Lys Ala Glu Asp Leu Ala Val Tyr
                100                 105                 110

Tyr Cys Gln Gln His Tyr Ser Tyr Pro Trp Thr Phe Gly Gly Gly Thr
            115                 120                 125

Lys Leu Glu Val Lys Arg Ala Asp Ala Ala Pro Thr Val Ser Ile Phe
            130                 135                 140

Pro Pro Ser Ser Glu Gln Leu Thr Ser Gly Gly Ala Ser Val Val Cys
145                 150                 155                 160

Phe Leu Asn
```

<210> SEQ ID NO 31
<211> LENGTH: 159
<212> TYPE: PRT
<213> ORGANISM: Mus musculus

<400> SEQUENCE: 31

```
Met Asp Met Arg Thr Pro Ala Gln Phe Leu Gly Ile Leu Leu Leu Trp
1               5                   10                  15

Phe Pro Gly Ile Lys Cys Asp Ile Lys Met Thr Gln Ser Pro Ser Ser
                20                  25                  30

Met Tyr Ala Ser Leu Gly Glu Arg Val Thr Phe Thr Cys Lys Ala Ser
            35                  40                  45

Gln Asp Ile Asn Ser Tyr Leu Ser Trp Phe Gln Gln Lys Pro Gly Lys
        50                  55                  60

Ser Pro Lys Thr Leu Ile Tyr Arg Ala Asn Arg Leu Val Asp Gly Val
65                  70                  75                  80

Pro Ser Arg Phe Ser Gly Ser Gly Ser Gly Gln Asp Tyr Ser Leu Thr
                85                  90                  95

Ile Ser Ser Leu Asp Tyr Glu Asp Met Gly Ile Tyr Tyr Cys Leu Gln
                100                 105                 110

Tyr Tyr Glu Phe Pro Leu Thr Phe Gly Ala Gly Thr Lys Leu Glu Leu
            115                 120                 125
```

Lys Arg Ala Asp Ala Ala Pro Thr Val Ser Ile Phe Pro Pro Ser Ser
            130                 135                 140
Glu Gln Leu Thr Ser Gly Gly Ala Ser Val Val Cys Phe Leu Asn
145                 150                 155

<210> SEQ ID NO 32
<211> LENGTH: 132
<212> TYPE: PRT
<213> ORGANISM: Artificial Sequence
<220> FEATURE:
<223> OTHER INFORMATION: Variable region of antibody

<400> SEQUENCE: 32

Met Arg Leu Leu Ala Gln Leu Leu Gly Leu Leu Met Leu Trp Val Pro
1               5                   10                  15
Gly Ser Ser Gly Asp Ile Val Met Thr Gln Thr Pro Leu Ser Ser Leu
            20                  25                  30
Val Thr Leu Gly Gln Pro Ala Ser Ile Ser Cys Arg Ser Ser Gln Ser
        35                  40                  45
Leu Val His Arg Asp Gly Asn Thr Tyr Leu Ser Trp Leu Gln Gln Arg
    50                  55                  60
Pro Gly Gln Pro Pro Arg Leu Leu Ile Tyr Lys Ile Ser Asn Arg Phe
65                  70                  75                  80
Phe Gly Val Pro Asp Arg Phe Ser Gly Ser Gly Ala Gly Thr Asp Phe
                85                  90                  95
Thr Leu Lys Ile Ser Arg Val Glu Ala Glu Asp Val Gly Val Tyr Tyr
            100                 105                 110
Cys Met Gln Ala Thr Gln Phe Pro His Thr Phe Gly Gln Gly Thr Lys
        115                 120                 125
Leu Glu Ile Lys
    130

<210> SEQ ID NO 33
<211> LENGTH: 20
<212> TYPE: DNA
<213> ORGANISM: Artificial Sequence
<220> FEATURE:
<223> OTHER INFORMATION: Syntheic DNA

<400> SEQUENCE: 33
cgggcggaaa aggccgacgc                                                   20

<210> SEQ ID NO 34
<211> LENGTH: 20
<212> TYPE: DNA
<213> ORGANISM: Artificial Sequence
<220> FEATURE:
<223> OTHER INFORMATION: Syntheic DNA

<400> SEQUENCE: 34
aggcccgcca tttcccgcgc                                                   20

<210> SEQ ID NO 35
<211> LENGTH: 20
<212> TYPE: PRT
<213> ORGANISM: Homo sapiens

<400> SEQUENCE: 35

Glu Asp Gly Val Thr Pro Tyr Met Ile Phe Phe Lys Asp Gly Leu Glu
1               5                   10                  15

```
<210> SEQ ID NO 36
<211> LENGTH: 172
<212> TYPE: PRT
<213> ORGANISM: Artificial Sequence
<220> FEATURE:
<223> OTHER INFORMATION: antibody

<400> SEQUENCE: 36

Met Ile Ile Tyr Arg Asp Leu Ile Ser His Asp Glu Met Phe Ser Asp
1               5                   10                  15

Ile Tyr Lys Ile Arg Glu Ile Ala Asp Gly Leu Cys Leu Glu Val Glu
            20                  25                  30

Gly Lys Met Val Ser Arg Thr Glu Gly Asn Ile Asp Asp Ser Leu Ile
        35                  40                  45

Gly Gly Asn Ala Ser Ala Glu Gly Pro Glu Gly Glu Gly Thr Glu Ser
    50                  55                  60

Thr Val Ile Thr Gly Val Asp Ile Val Met Asn His His Leu Gln Glu
65                  70                  75                  80

Thr Ser Phe Thr Lys Glu Ala Tyr Lys Lys Tyr Ile Lys Asp Tyr Met
                85                  90                  95

Lys Ser Ile Lys Gly Lys Leu Glu Glu Gln Arg Pro Glu Arg Val Lys
            100                 105                 110

Pro Phe Met Thr Gly Ala Ala Glu Gln Ile Lys His Ile Leu Ala Asn
        115                 120                 125

Phe Lys Asn Tyr Gln Phe Phe Ile Gly Glu Asn Met Asn Pro Asp Gly
    130                 135                 140

Met Val Ala Leu Leu Asp Tyr Arg Glu Asp Gly Val Thr Pro Tyr Met
145                 150                 155                 160

Ile Phe Phe Lys Asp Gly Leu Glu Met Glu Lys Cys
                165                 170

<210> SEQ ID NO 37
<211> LENGTH: 20
<212> TYPE: PRT
<213> ORGANISM: Homo sapiens

<400> SEQUENCE: 37

Met Tyr Arg Met Gln Leu Leu Ser Cys Ile Ala Leu Ser Leu Ala Leu
1               5                   10                  15

Val Thr Asn Ser
            20
```